(12) United States Patent
Seki et al.

(10) Patent No.: US 8,010,178 B2
(45) Date of Patent: Aug. 30, 2011

(54) BIOMAGNETIC FIELD MEASUREMENT APPARATUS HAVING A PLURALITY OF MAGNETIC PICK-UP COILS

(75) Inventors: Yusuke Seki, Musashino (JP); Akihiko Kandori, Tokyo (JP); Mitsuru Oonuma, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 956 days.

(21) Appl. No.: 11/905,682

(22) Filed: Oct. 3, 2007

(65) Prior Publication Data
US 2008/0084204 A1    Apr. 10, 2008

(30) Foreign Application Priority Data
Oct. 5, 2006    (JP) .................................. 2006-273566

(51) Int. Cl.
*A61B 5/05* (2006.01)
(52) U.S. Cl. ........................................ 600/409; 324/300
(58) Field of Classification Search .......... 600/409–411, 600/415; 324/300, 301, 244, 248, 260, 261
See application file for complete search history.

(56) References Cited

U.S. PATENT DOCUMENTS
6,275,719 B1    8/2001    Kandori et al.
6,370,414 B1    4/2002    Robinson FOREIGN PATENT DOCUMENTS
JP    7-297456    4/1994
JP    11253412 A *    9/1999
JP    2002-336211    5/2001

OTHER PUBLICATIONS

Williamson, S.J. and Kaufman, L., "*Biomagnetism*", Journal of Magnetism and Magnetic Materials, vol. 22, 1981, pp. 129-201.
Hosaka, H. and Cohen, D., "*Part IV Visual Determination of Generators of the Magnetocardiogram*", J. Electrocadiology, vol. 9 No. 4, 1976, pp. 426-432.
A corrected European Search Report dated Dec. 22, 2008 which replaces an extended European Search Report dated Oct. 9, 2008, regarding European Application No. 07019302.4-1265 / 1911398.
Buchanan, D.S., et al., "Instrumentation for Clinical Applications of Neuromagnetism", Advances in Cryogenic Engineering Proceedings of the Cryogenic Engineering Conference, vol. 33, No. 1, Jun. 1, 1987, pp. 97-106.
Extended European Search Report dated Oct. 9, 2008 regarding European Application No. 07019302.4-1265 / 1911398.
Buchanan, D.S., et al., "Instrumentation for Clinical Applications of Neuromagnetism", Neuromagnetism Laboratory Department of Physics, New York University, New York, New York, XP008096991, pp. 97-106, 1988.

* cited by examiner

*Primary Examiner* — Parikha S Mehta
(74) *Attorney, Agent, or Firm* — Stites & Harbison PLLC; Juan Carlos A. Marquez, Esq.

(57) ABSTRACT

A biomagnetic field measurement apparatus capable of easily bringing the sensor planes close to the head surface of the subject and capable of detecting cerebral magnetic fields of the left brain and the right brain simultaneously with a higher sensitivity is provided by disposing two independent cryostats holding SQUID fluxmeters in the mirror image relation to each other. The two cryostats move vertically and horizontally and rotate while interlocking with each other and maintaining the mirror image relation to each other. A gantry holding the cryostats has a function of suppressing vibration of the cryostats and has a gate shape.

16 Claims, 23 Drawing Sheets

BIOMAGNETIC FIELD MEASUREMENT APPARATUS HAVING A PLURALITY OF MAGNETIC PICK-UP COILS

INCORPORATION BY REFERENCE

The present application claims priority from Japanese application JP2006-273566 filed on Oct. 5, 2006, the content of which is hereby incorporated by reference into this application.

BACKGROUND OF THE INVENTION

The present invention relates to a biomagnetic field measurement apparatus intended to detect a magnetic field mainly generated from a brain.

In a magnetoencephalograph for measuring a magnetic field (cerebral magnetic field) generated from a brain, a large number of pick-up coils are arranged over the whole-head surface with the object of mapping the electrophysiological activity of cerebral nerves. The magnetoencephalograph of this kind is called whole-head type magnetoencephalograph because the pick-up coils are arranged so as to cover the whole head for the purpose of measurement (see, for example, Patent Document 1). A merit of the whole-head type magnetoencephalograph is that signals of the whole cerebral hemisphere can be measured simultaneously. In other words, mapping of exciting regions becomes possible. For example, abnormally exciting regions in epilepsy can be discriminated by mapping the exciting regions.

There is also an example in which a plurality of adiabatic mechanisms each including means for measuring biomagnetism such as a SQUID sensor are arranged and the adiabatic mechanisms are driven respectively singly (Patent Document 2).

In the conventional biomagnetic field measurement apparatus used for magnetocardiography measurement or magnetoencephalography measurement, a method of detecting magnetic signals of an object living body by using pick-up coils each formed of a superconducting wire and transmitting the magnetic signals to superconducting quantum interference devices (hereafter abbreviated to SQUIDs) is adopted. The pick-up coils have the function of removing noise caused by an environmental magnetic field and improving the signal to noise ratio. As for the biomagnetic measurement and the pick-up coils, there is detailed description in Non-Patent Document 1.
[Patent Document 1] JP-A-07-297456
[Patent Document 2] JP-A-2002-336211
[Non-Patent Document 1] S. J. Williamson and L. Kaufman, Journal of Magnetism and Magnetic Materials 22 (1981), 129-201.

SUMMARY OF THE INVENTION

The whole-head type magnetoencephalograph has a merit that measurement over a wide area of the whole brain can be conducted at a time. A cryostat for fixing a SQUID fluxmeter and keeping it at low temperatures is designed to fit the standard human head. Therefore, the distance between the sensor and the head surface cannot be regulated. This poses a problem that the signal strength decreases or measurement cannot be conducted. Furthermore, there is a problem that only partial information is obtained fragmentarily even if a plurality of sensors are driven individually and sufficient measurement cannot be conducted.

A conventional differential type magnetic pick-up coil has only a configuration for detecting a magnetic field differentiated in one certain direction as described in Non-Patent Document 1 (FIG. 5). In this method, there is a problem that the environmental magnetic field is not weakened sufficiently in the case where the environmental magnetic field is strong as in the magnetic shieldless environment. For weakening the environmental magnetic field, there is a method of raising the degree of the differential type magnetic pick-up coil. In this method, there is a problem that the magnetic signal which is a detection object is also weakened although the environmental magnetic field is weakened.

In view of the problems, the present invention provides a biomagnetic field measurement apparatus capable of detecting a cerebral magnetic field with a higher sensitivity and more simply than the conventional art. Specifically, an object of the present invention is to provide a biomagnetic field measurement apparatus capable of easily bringing a sensor face close to a head surface of a subject by interlocking two independent cryostats with a mirror image relation maintained between and detecting cerebral magnetic fields of the right brain and the left brain simultaneously with high sensitivity.

In the biomagnetic field measurement apparatus according to the present invention, two independent cryostats holding SQUID fluxmeters are disposed so as to be in the mirror image relation to each other. A pick-up sensor is provided in each cryostat with a part thereof projected from the inside of the cryostat in a side face direction.

The two cryostats move vertically and horizontally and rotate while interlocking with each other and maintaining the mirror image relation to each other.

A gantry holding the cryostats has a function of suppressing vibration of the cryostats and has a gate shape.

The gantry has a mechanism for electrically driving the cryostats. The gantry also has a saving lever for making it possible to widen the spacing between the two cryostats manually at all times.

The gantry includes six supports. A first support is a gate type support for supporting the whole gantry. A second support is supported by the first support and driven in the vertical direction. Third and fourth supports are supported by the second support. The third and fourth supports can move in the horizontal direction when seen from the second support. The third and fourth supports are interlocked with each other and driven in directions that are opposite to each other. A fifth support is supported by the third support to support a first cryostat and driven to rotate around an axis of the first cryostat. A sixth support is supported by the fourth support to support a second cryostat and driven to rotate around an axis of the second cryostat. The fifth and sixth supports are interlocked with each other and rotated in directions that are opposite to each other.

A cover in the front of the gantry can be opened and closed by using a hinge structure in order to conduct maintenance work such as liquid helium supply, vacuum drawing on the cryostats and sensor exchange efficiently.

Surfaces of the two cryostats are coated with a conductive paint in order to shield electromagnetic waves.

Each of the two cryostats has a distance sensor for sensing a distance between cryostat surfaces in the vicinity of detection faces of magnetic sensors.

In each of the two cryostats, a pressure sensor for sensing pressure applied to the cryostat surface is provided on the cryostat surface in the vicinity of the detection face of magnetic sensor.

According to the present invention, it becomes possible to provide a biomagnetic field measurement apparatus capable of detecting cerebral magnetic fields with higher sensitivity and more ease as compared with the conventional art.

Other objects, features and advantages of the invention will become apparent from the following description of the embodiments of the invention taken in conjunction with the accompanying drawings.

BRIEF DESCRIPTION OF THE DRAWINGS

FIGS. 2A-2F are six-direction views showing the magnetic field measurement apparatus in the embodiment, in which FIG. 2A is a front view, FIG. 2B is a back view, FIG. 2C is a left side view (left side viewed from the front side), FIG. 2D is a right side view (right side viewed from the front side), FIG. 2E is a top view, and FIG. 2F is a bottom view;

FIGS. 15A and 15B are oblique views showing a movement of the gantry at time of cryostat maintenance in the embodiment, in which FIG. 15A is a view showing a state in which a second support 106 is lowered most, and FIG. 15B is a view showing a state in which a gantry front cover 105 is opened;

DESCRIPTION OF THE EMBODIMENTS

Figure 1:
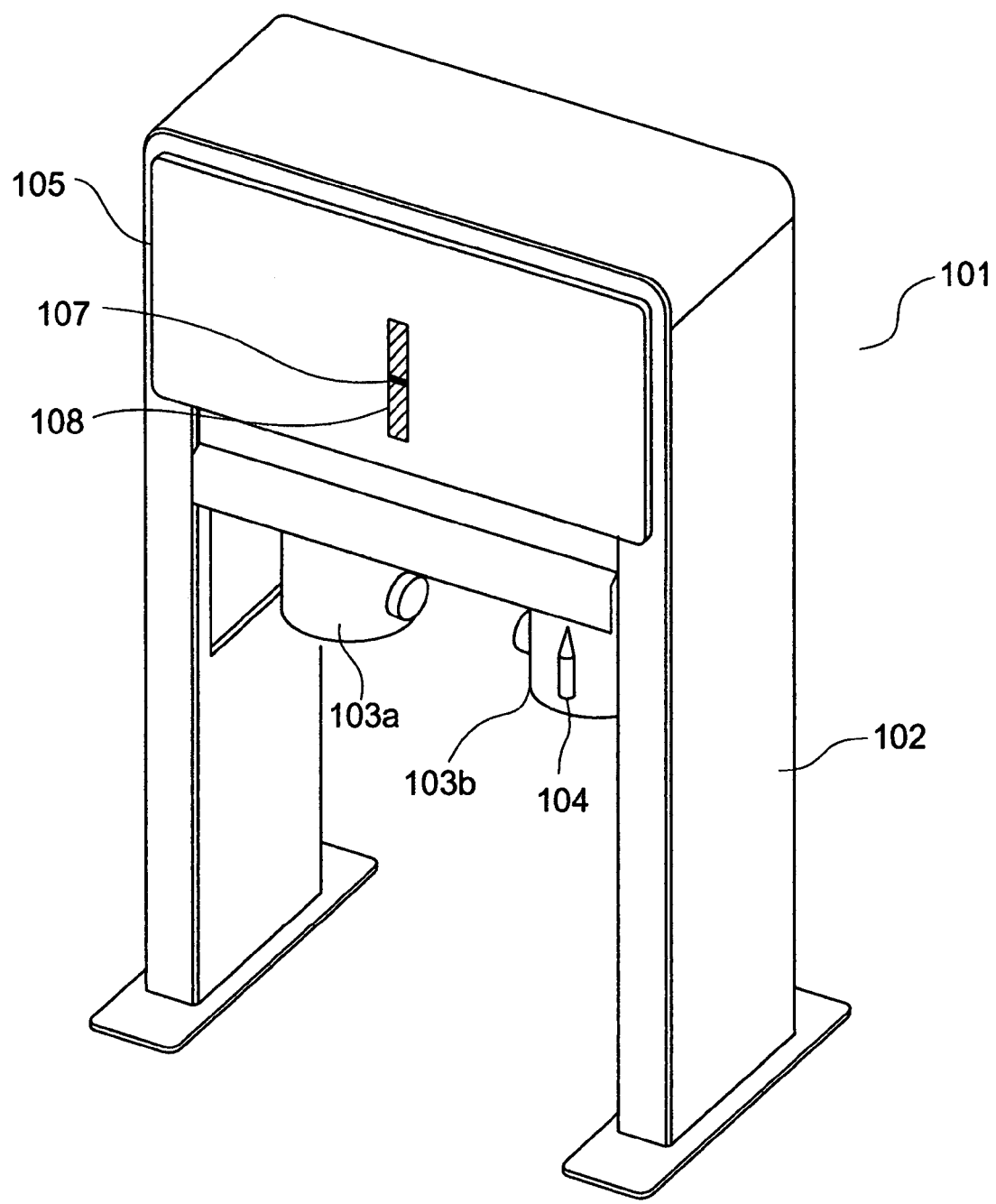
FIG. 1 is an oblique view showing a magnetic field measurement apparatus in an embodiment.

Hereafter, an embodiment of the present invention will be described in detail with reference to the drawings. In the drawings, components having the same function are denoted by like reference characters.

As a superconducting material forming pick-up coils used in the apparatus in the embodiment described hereafter, a low temperature superconducting material having a low temperature superconducting transition temperature and acting as a superconductor at a low temperature (for example, the liquid helium temperature), or a high temperature superconducting material having a high temperature superconducting transition temperature and acting as a superconductor at a high temperature (for example, the liquid nitrogen temperature) can be used. A superconducting material having a superconducting transition temperature between the liquid helium temperature and the liquid nitrogen temperature, or a superconducting material having a superconducting transition temperature higher than the liquid nitrogen temperature may also be used. As for the material forming the pick-up coils, metal having a high electrical conductivity such as copper can also be used.

Figure 2A:
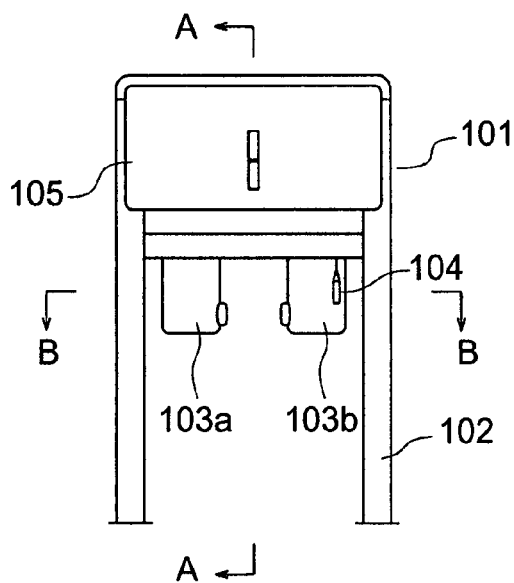
Figure 2B:
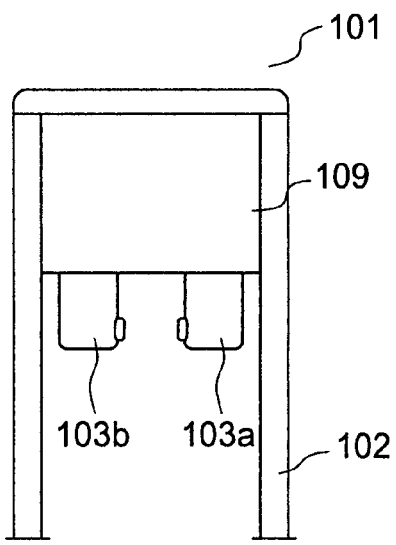
Figure 2D:
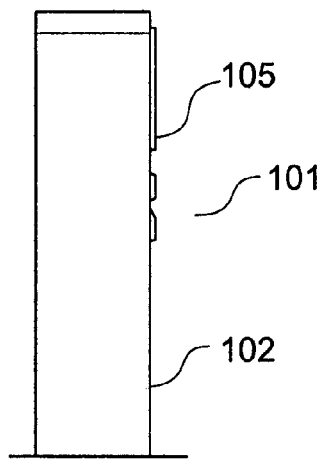
Figure 2C:
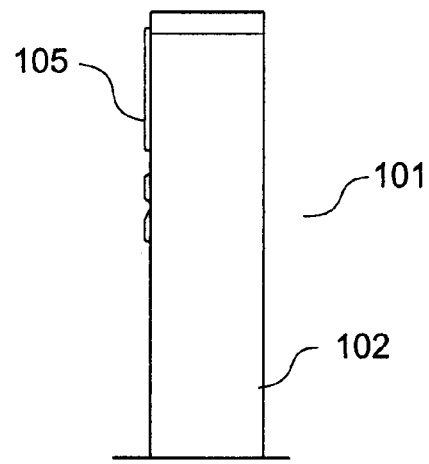
Figure 2E:
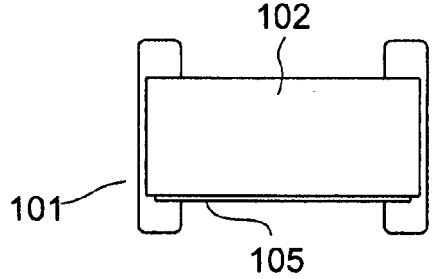
Figure 2F:
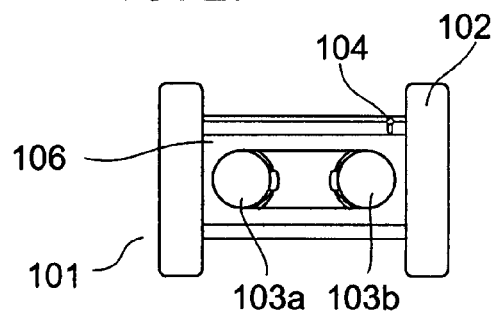
Figure 3A:
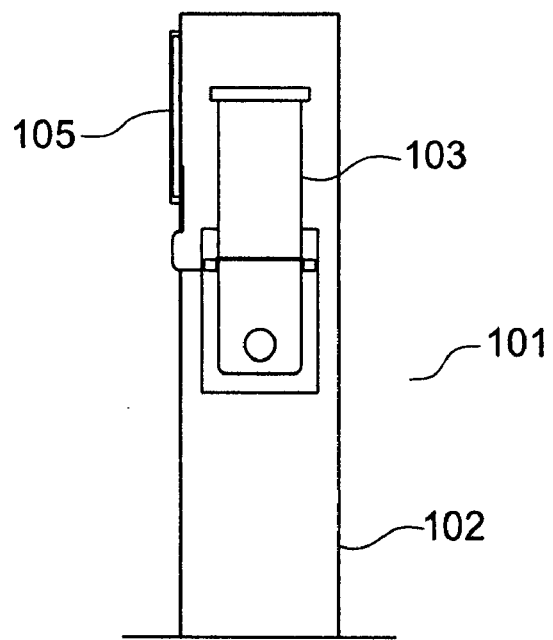
FIGS. 3A-3C are sectional views showing the magnetic field measurement apparatus in the embodiment.
Figure 3B:
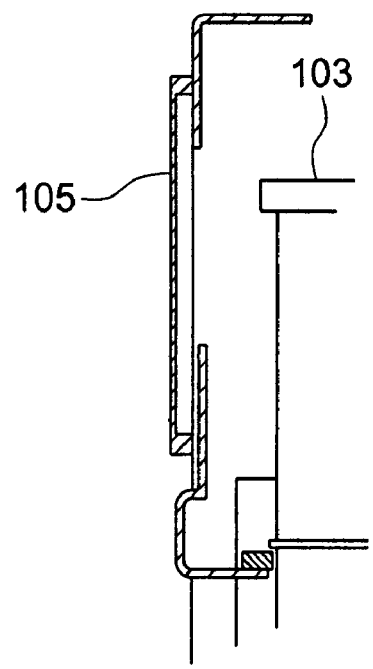
Figure 3C:
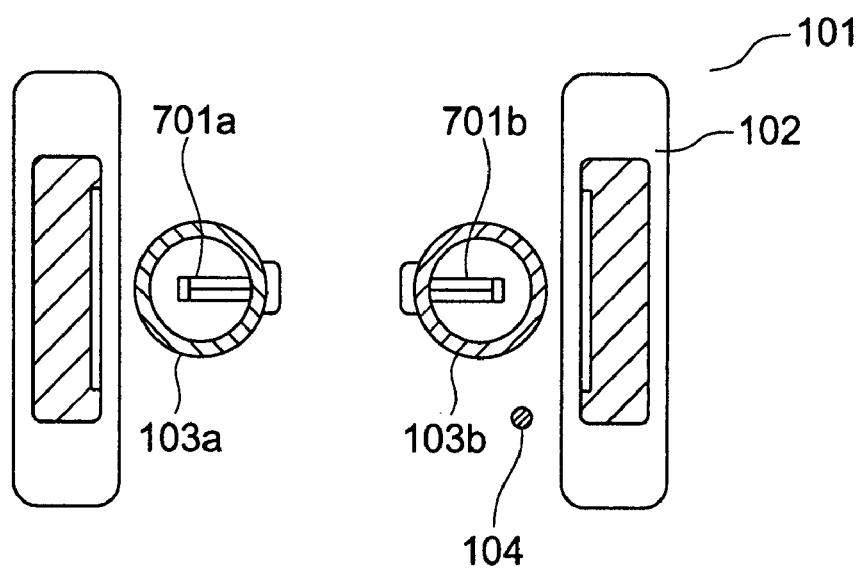

FIG. 1 is an oblique view showing a magnetic field measurement apparatus in the present embodiment. FIGS. 2A-2F are six-direction views showing the magnetic field measurement apparatus in the embodiment, in which FIG. 2A is a front view, FIG. 2B is a back view, FIG. 2C is a left side view (left side viewed from the front side), FIG. 2D is a right side view (right side viewed from the front side), FIG. 2E is a top view, and FIG. 2F is a bottom view. FIGS. 3A-3C are sectional views showing the magnetic field measurement apparatus in the embodiment, in which FIG. 3A is a sectional view taken along an A-A section in FIG. 2A, FIG. 3B is a sectional view with neighborhood of a gantry front cover 105 is enlarged, and FIG. 3C is a sectional view taken along a B-B section in FIG. 2A.

A magnetic field measurement apparatus 101 includes cryostats 103a and 103b each for keeping a SQUID fluxmeter at low temperatures and fixing it, and a gantry for supporting and driving the cryostats 103a and 103b. A gate type support 102 is a part of a structure of the gantry, and the gate type support 102 supports the whole gantry. The gate type support 102 can hold down vibration of the gantry by its gate type structure. Holding down the vibration of the gantry brings about an effect that vibration of SQUID fluxmeters held in the cryostats 103a and 103b is held down and magnetic noise caused by the vibration is reduced. A lever 104 is means for moving the cryostat 103b to the left or right manually.

A gantry front cover 105 is a part of the structure of the gantry, and it can be opened and closed by its hinge structure. Typically, the magnetic field measurement apparatus 101 is used with the gantry front cover 105 closed. When conducting maintenance work of the cryostats 103a and 103b, however, the gantry front cover 105 is kept in the open state. Since the hinge structure is adopted, it is not necessary to remove the whole gantry front cover 105. This brings about an effect that the maintenance work can be conducted efficiently.

A cryostat location indication 107 is disposed in a central location of the gantry front cover 105 in the horizontal direction. The cryostat location indication 107 moves in the vertical direction while being interlocked with the movement of the cryostats 103a and 103b in the vertical direction. Owing to this configuration, the cryostat location indication 107 has a function of indicating the location of the cryostats 103a and 103b in the vertical direction. In addition, the cryostat location indication 107 has also a function of indicating the center of the two cryostats 103a and 103b in the horizontal direction. Typically, the subject is disposed in the center location of the two cryostats 103a and 103b in the horizontal direction at the time of measurement. If the center location of the two cryostats 103a and 103b in the horizontal direction can be confirmed easily, the effect of facilitating the positioning of the subject is brought about. In the oblique view shown in FIG. 1, parallel oblique lines in a transparent member 108 are not lines appearing as the external appearance, but they represent that the portion is transparent for convenience.

It is desirable that all of the gantry and the cryostats included in the magnetic field measurement apparatus 101 are formed of non-magnetic materials. In the present embodiment, the gantry is formed of aluminum and brass, and the cryostats are formed of FRP (fiber reinforced plastics).

Figure 4:
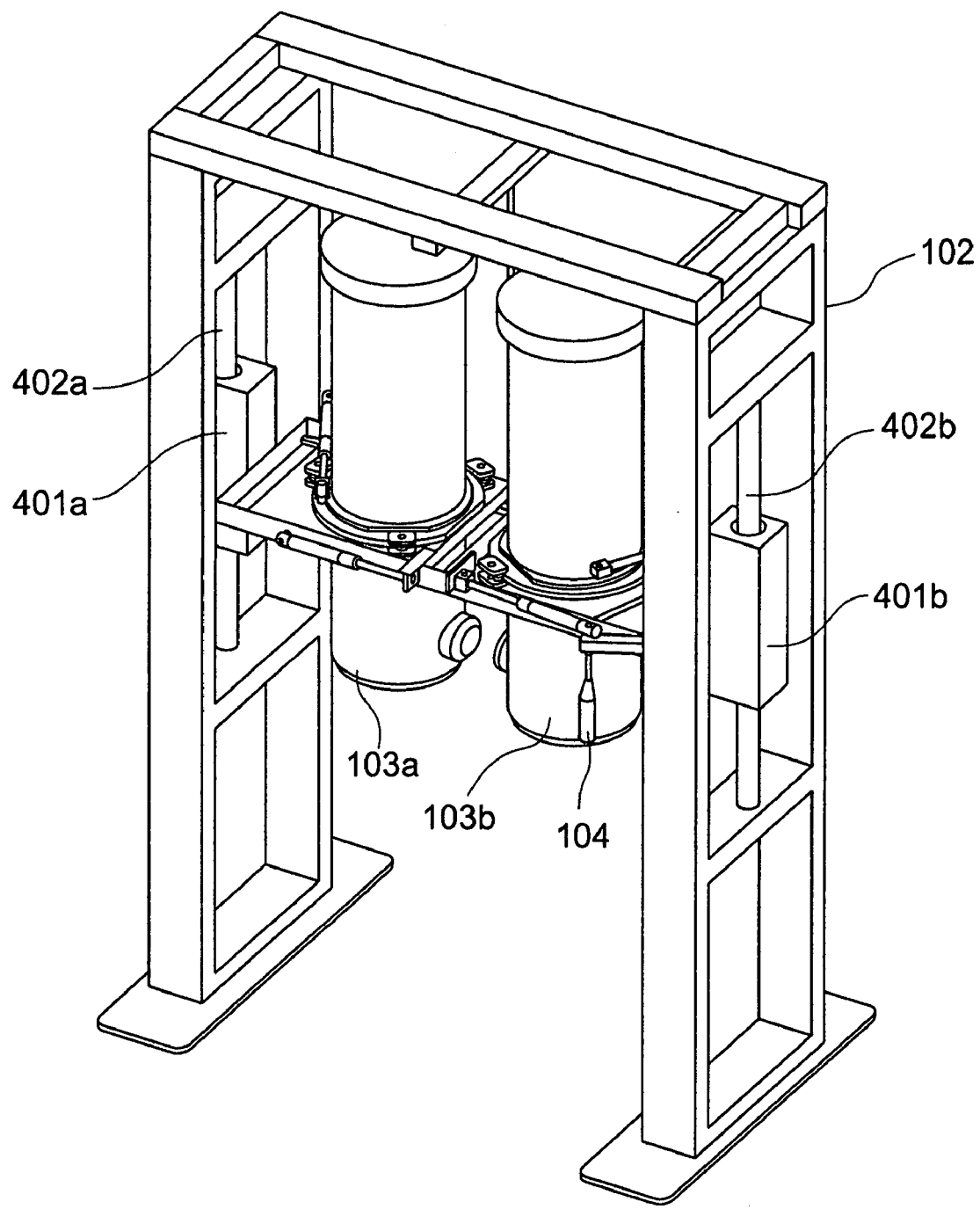
FIG. 4 is a diagram showing a detailed structure of a gantry in the embodiment.
Figure 5:
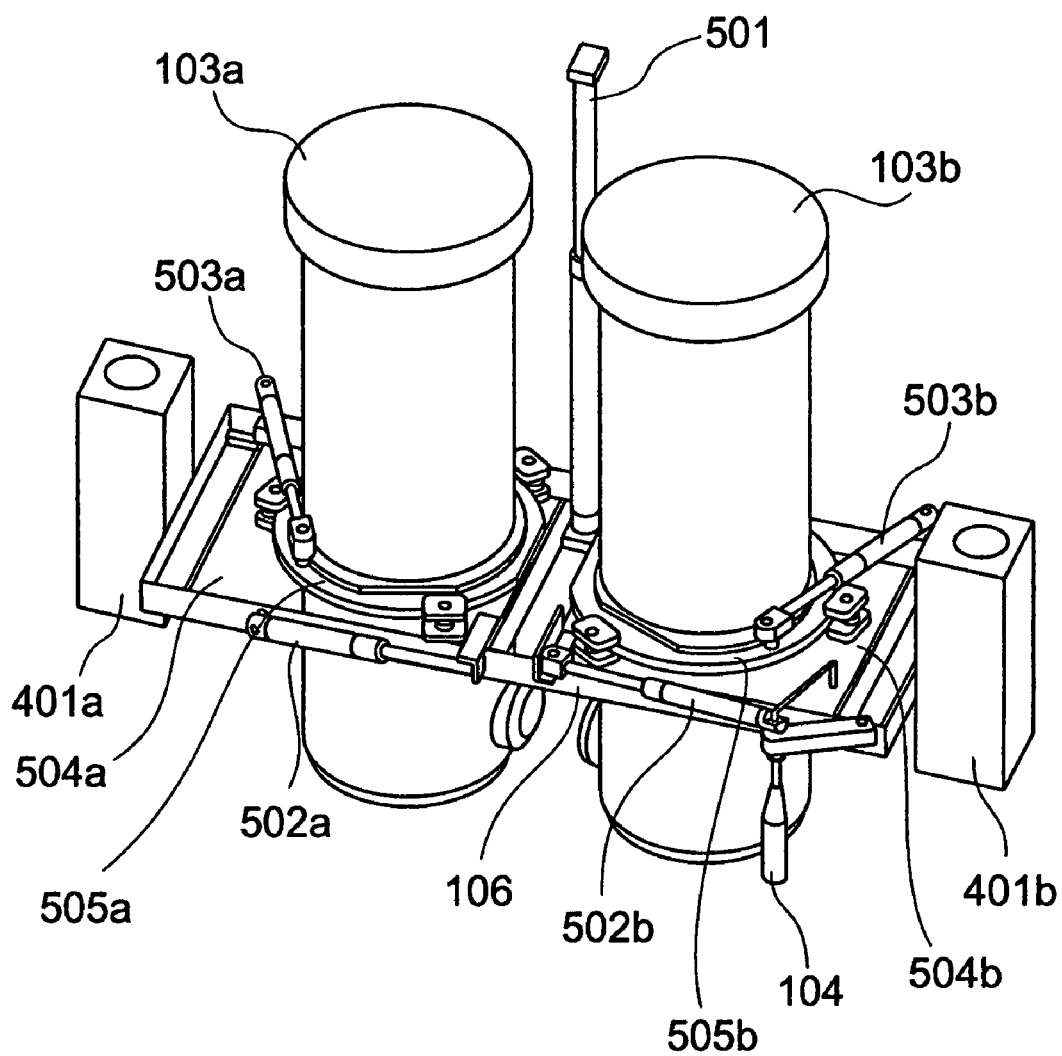
FIG. 5 is a diagram showing a detailed structure of a gantry in the embodiment.

FIGS. 4 and 5 are diagrams showing a detailed structure of the gantry in the present embodiment. The gate type support 102 is fixed to the floor surface, and the gate type support 102 supports the whole gantry. The first support (gate type support) 102 drives a second support 106 in the vertical direction (upward or downward direction) by using drive means 501. Guide mechanisms 401a and 401b are fixed to ends of the second support 106. The guide mechanisms 401a and 401b move respectively along rails 402a and 402b fixed to leg parts of the gate type support 102. As a result, the second support 106 can move in the vertical direction smoothly. In addition, the second support 106 drives a third support 504a in the horizontal direction (left or right direction) by using drive means 502a and drives a fourth support 504b in the horizontal direction (left or right direction) by using drive means 502b. The third support 504a and the fourth support 504b are interlocked with each other and driven in directions that are opposite to each other. In other words, the third support 504a and the fourth support 504b are interlocked with each other and driven at the same velocity in directions that they get nearer to each other or in directions that they go away from each other. The third support 504a drives a fifth support 505a to rotate it (clockwise or counterclockwise) in the horizontal plane by drive means 503a. In the same way, the fourth support 504b drives a sixth support 505b to rotate it (clockwise or counterclockwise) in the horizontal plane by drive means 503b. The fifth support 505a and the sixth support 505b are interlocked with each other and driven to rotate in directions that are opposite to each other at the same rotation velocity. In addition, the cryostat 103a is fixed by the fifth support 505a, and the cryostat 103b is fixed by the sixth support 505b.

Each of the drive means 501, 502a, 502b, 503a and 503b has a sensor for measuring the drive quantity. Thus, the location and rotation angle of each of the cryostats 103a and 103b can be monitored. By recording drive quantities of respective drive means at a certain measurement time, arrangement of the cryostats 103a and 103b at the time of the measurement can be reproduced.

Owing to the configuration heretofore described, the two cryostats 103a and 103b can move in parallel in the upward or downward (vertical) direction and left or right (horizontal) direction and rotate around vertical axes of the cryostats, in synchronism while maintaining the bilateral symmetry relation. Since the two cryostats 103a and 103b are thus interlocked with each other and moved in the vertical, lateral and rotational directions in synchronism with the bilateral symmetry relation maintained, pick-up planes 604a and 604b (see FIG. 13A) are always interlocked with each other with the bilateral symmetry relation maintained. As a result, it becomes unnecessary to square locations of the two pick-up planes 604a and 604b individually with locations of parts to be measured (typically the head of the subject). Furthermore, since the cryostats are necessarily in the bilateral symmetry relation, it becomes possible to easily square locations of the pick-up planes 604a and 604b with locations of regions that are bilaterally symmetrical in the head. According to this configuration, it becomes possible to measure magnetoencephalography signals in corresponding regions in the left brain and the right brain simultaneously. In other words, the present configuration brings about an effect that not only the time required to square the locations of the pick-up planes with the locations of the parts to be measured becomes short but also the precision of the location registration is improved.

The lever 104 is means for moving the cryostat 103b to the left or right manually. Usually, the magnetic field measurement apparatus is used with the lever 104 pressed to the back. However, the third support 504a can be moved rightward manually by pulling the lever 104 near side as occasion demands. On the contrary, the third support 504a can be moved leftward manually by pressing the lever 104 to the back from the state in which it is pulled near side. In other words, if the lever 104 is pulled near side, the cryostat 103b moves rightward. As a result, the spacing between the cryostats 103a and 103b becomes great. If the lever 104 is pressed to the back, the cryostat 103b moves leftward. As a result, the spacing between the cryostats 103a and 103b becomes small. It becomes possible by using the lever 104 to manually regulate the spacing between the cryostats 103a and 103b finely or manually increasing the spacing between the cryostats 103a and 103b.

Figure 6:
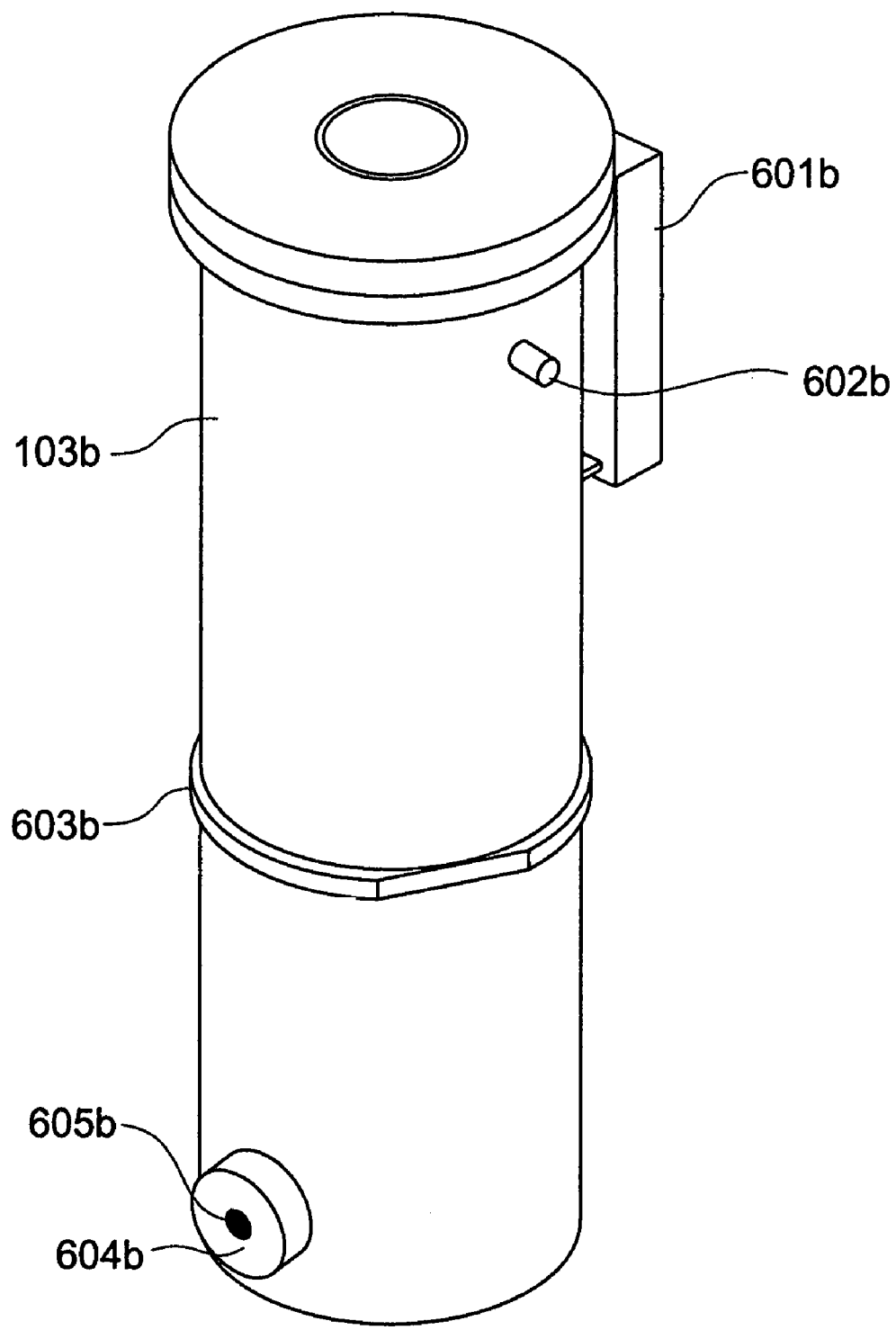
FIG. 6 is an oblique view showing a cryostat in the embodiment.
Figure 7A:
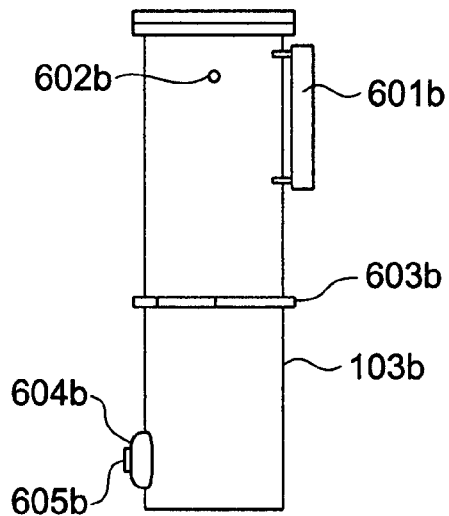
FIGS. 7A-7F are six-direction views showing a cryostat in the embodiment.
Figure 7B:
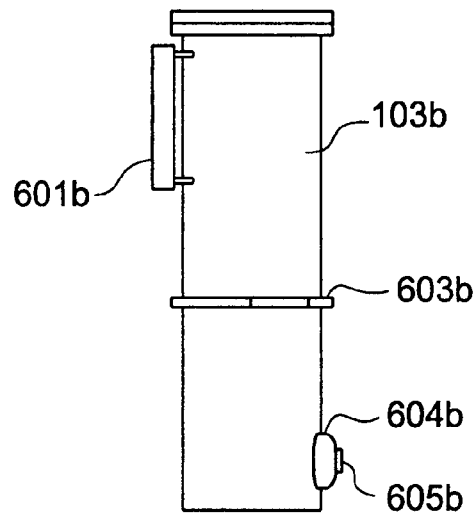
Figure 7C:
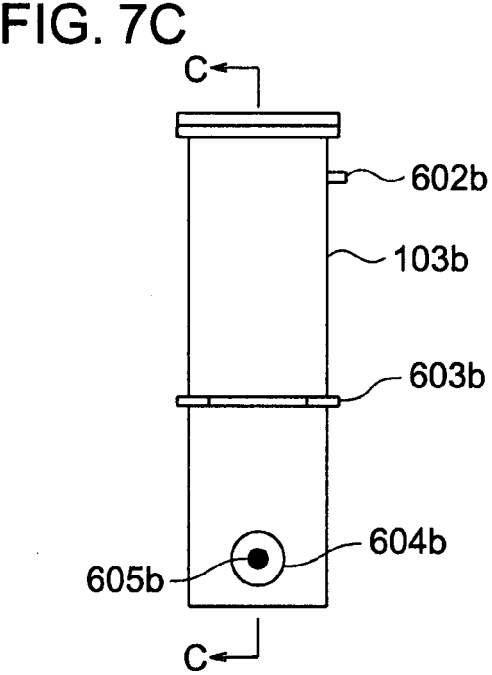
Figure 7D:
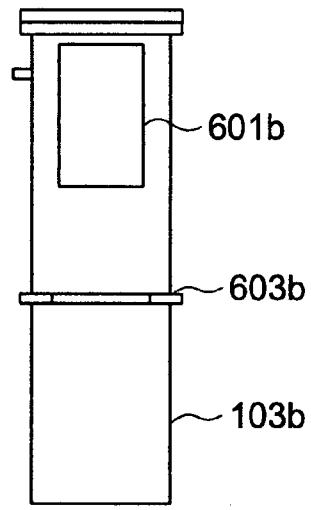
Figure 7E:
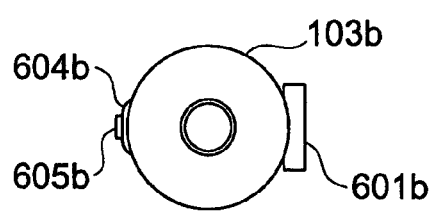
Figure 7F:
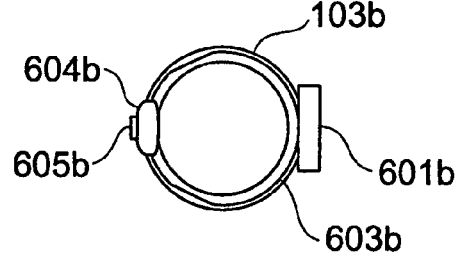

FIG. 6 is an oblique view showing a cryostat in the present embodiment. FIGS. 7A-7F are six-direction views showing a cryostat in the present embodiment. In FIG. 6 and FIGS. 7A-7F, the cryostat 103b included in the pair of cryostats and disposed on the right side when seen from the front is shown. The cryostat 103a disposed on the left side when seen from the front is in the bilateral symmetry relation with the cryostat 103b. In FIGS. 7A-7F, FIG. 7A is a front view, FIG. 7B is a back view, FIG. 7C is a left side view (a view seen from the left side), FIG. 7D is a right side view (a view seen from the right side), FIG. 7E is a top view, and FIG. 7F is a bottom view.

The cryostat 103b is a vacuum adiabatic receptacle. The inside of the cryostat 103b is filled with liquid helium. The cryostat 103b is used to hold a SQUID fluxmeter at low temperatures. An FLL circuit 601b for driving the SQUID fluxmeter is fixed to a side face of the cryostat 103b. If a cable connecting the SQUID fluxmeter to the FLL circuit is long, a signal is attenuated and noise is apt to get on the cable. Therefore, it is desirable that the cable is as short as possible. In the present embodiment, the cable connecting the SQUID fluxmeter to the FLL circuit can be made short by fixing the FLL circuit 601b to the side face of the cryostat 103b. A vacuum drawing port 602b is disposed so as to be in the front location in the state in which the cryostat 103b is fixed to the gantry. As a result, vacuum drawing work can be conducted in the state in which the cryostat 103b is fixed on the gantry. The cryostat 103b is fixed to the gantry and driven by fixing an intermediate flange 603b to the sixth support 505b (see FIG. 5).

A pick-up coil of the SQUID fluxmeter is fixed within the cryostat 103b near the pick-up plane 604b. As shown in FIG. 6, the pick-up plane 604b is provided with a shape projected from the side face of the cryostat 103b. This brings about an effect that it becomes possible to easily square the pick-up plane 604b with the measurement location of the head and sense of oppression upon the subject is also alleviated. The thickness of a vacuum layer, a Dewar outer layer and a Dewar inner layer between the pick-up coil and the pick-up plane 604b can be made small by making the area of the pick-up plane 604b small. This brings about an effect that the distance between a signal source and the pick-up coil becomes small and the signal strength becomes great.

The surface of the cryostat 103b is coated with a conductive paint containing metal having a high electric conductivity such as silver. This conductive paint has an effect of shielding an electromagnetic wave. The electromagnetic wave not only forms environmental noise, but also brings about a bad influence of degrading the SQUID detection sensitivity. In the conventional art, the electromagnetic wave is shielded by placing the cryostat in a magnetic shield room formed of Permalloy or aluminum. On the other hand, in the present embodiment, it becomes possible to shield the electromagnetic wave without using the magnetic shield room by providing the cryostat itself with the function of shielding the electromagnetic wave. Furthermore, the conductive paint applied to the cryostat 103b can be connected to the ground of the FLL circuit 601b by fixing the FLL circuit 601b to the cryostat 103b with a screw of non-magnetic metal such as brass or SUS. As a result, it becomes possible that the conductive paint functions as the electromagnetic wave shield substance stably.

Figure 8:
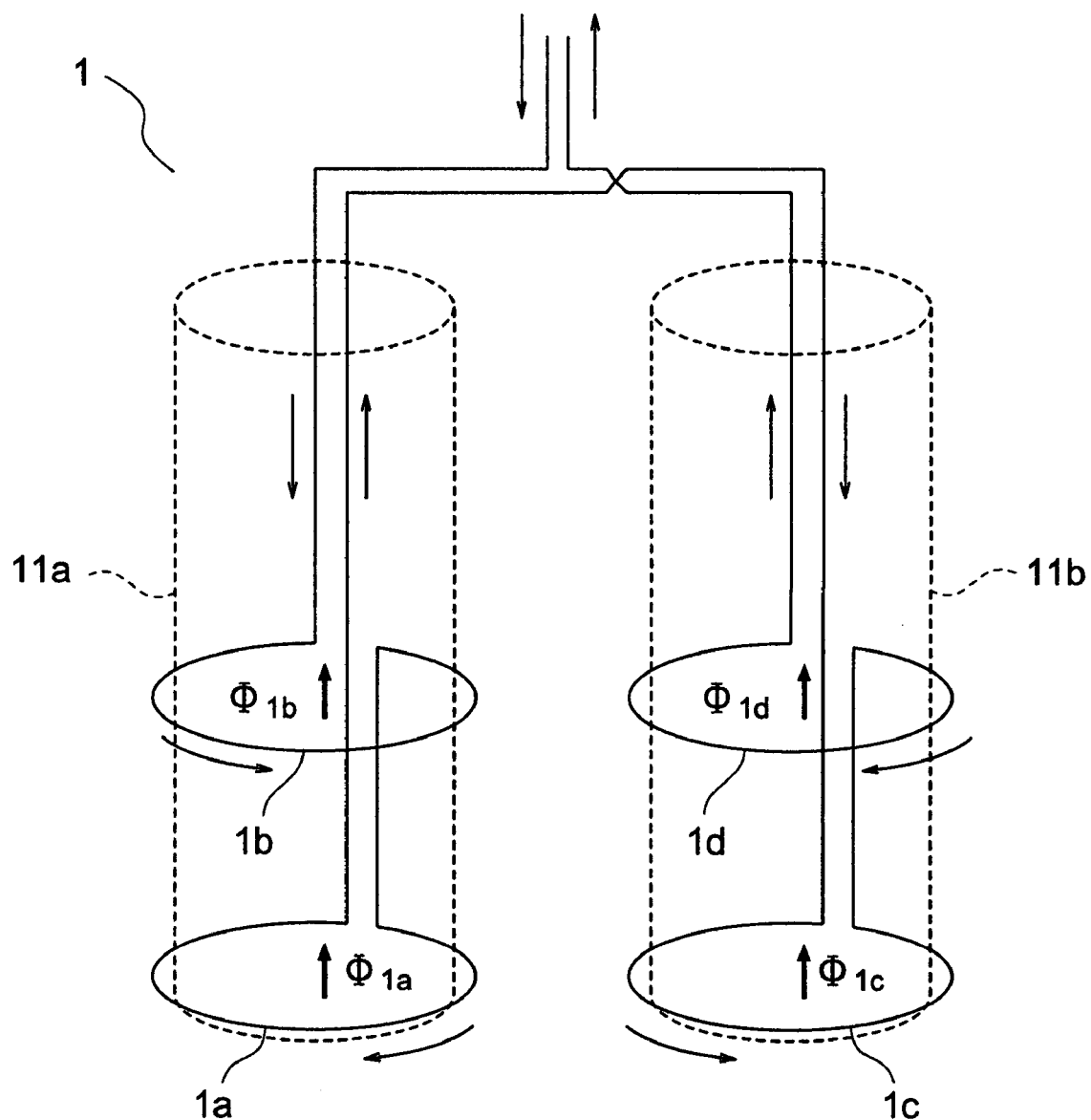
FIG. 8 is a first oblique view showing a pick-up coil in the embodiment.

FIG. 8 is an oblique view showing a pick-up coil in the present embodiment.

A pick-up coil 1 includes a coil 1a formed by winding one turn of a superconducting wire material round a bobbin 11a in a first direction, a coil 1b formed by winding one turn in a second direction opposite to the first direction at a predetermined distance in the vertical direction from the coil 1a, a coil 1c formed by winding one turn of the superconducting wire material round a bobbin 11b, which is disposed at a predetermined distance in the horizontal direction from the coil 1a, in the second direction, and a coil 1d formed by winding one turn in the first direction at the predetermined distance in the vertical direction from the coil 1c. In other words, the pick-up coil 1 is formed of one wire. The coil 1a and the coil 1c are on the same plane, and the coil 1b and the coil 1d are on the same plane. In other words, a plurality of first-order differential coils are disposed in parallel at the predetermined spacing. In this configuration, magnetic flux $\Phi_{P1}$ detected by the pick-up coil 1 can be represented by the following (Expression 1)

$$\Phi_{P1}=(\Phi_{1a}-\Phi_{1b})-(\Phi_{1c}-\Phi_{1d}) \quad \text{(Expression 1)}$$

where $\Phi_{1a}$ is magnetic flux piercing the coil 1a, $\Phi_{1b}$ is magnetic flux piercing the coil 1b, $\Phi_{1c}$ is magnetic flux piercing the coil 1c, and $\Phi_{1d}$ is magnetic flux piercing the coil 1d.

In other words, the pick-up coil 1 in the present embodiment is a pick-up coil that conducts the first-order differential in an axis direction (vertical direction) of the bobbins 11a (the first term) and 11b (the second term) and simultaneously conducts the first-order differential in the horizontal direction. In this way, the pick-up coil 1 detects the magnetic signal subjected to the first-order differential in the vertical direction and in addition subjected to the first-order differential in the horizontal direction. Therefore, the environmental magnetic field can be reduced as compared with the case where the first-order differential type pick-up coil is used.

Figure 9:
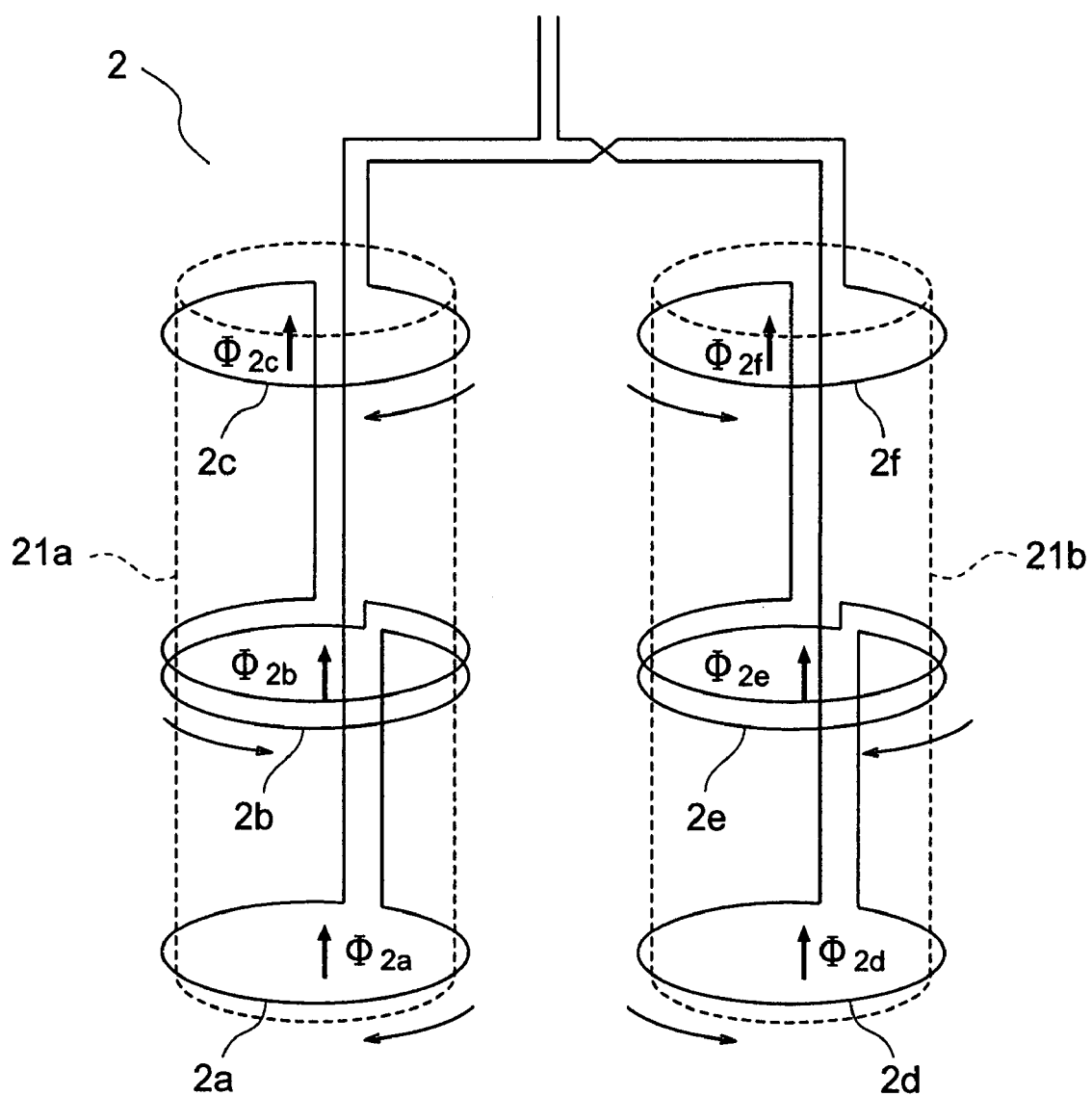
FIG. 9 is a second oblique view showing a pick-up coil in the embodiment.

FIG. 9 is an oblique view showing a pick-up coil in the present embodiment.

A pick-up coil 2 in the present embodiment includes a coil 2a formed by winding one turn of a superconducting wire material round a bobbin 21a in a first direction, a coil 2b formed by winding two turns in a second direction opposite to the first direction at a predetermined distance in the vertical direction from the coil 2a, a coil 2c formed by winding one turn in the first direction further at a predetermined distance in the vertical direction from the coil 2b, a coil 2d formed by winding one turn of the superconducting wire material round a bobbin 21b, which is disposed at a predetermined distance in the horizontal direction from the coil 2a, in the second direction, a coil 2e formed by winding two turns in the first direction at a predetermined distance in the vertical direction from the coil 2d, and a coil 2f formed by winding one turn in the second direction further at a predetermined distance in the vertical direction from the coil 2e. In other words, the pick-up coil 2 is formed of one wire. The coil 2a and the coil 2d are on the same plane, the coil 2b and the coil 2e are on the same plane, and the coil 2c and the coil 2f are on the same plane. In other words, a plurality of second-order differential coils are disposed in parallel at the predetermined spacing. In this configuration, magnetic flux $\Phi_{P2}$ detected by the pick-up coil 2 can be represented by the following (Expression 2)

$$\Phi_{P2}=(\Phi_{2a}-2\Phi_{2b}+\Phi_{2c})-(\Phi_{2d}-2\Phi_{2e}+\Phi_{2f}) \quad \text{(Expression 2)}$$

where $\Phi_{2a}$ is magnetic flux piercing the coil 2a, $\Phi_{2b}$ is magnetic flux piercing the coil 2b, $\Phi_{2c}$ is magnetic flux piercing the coil 2c, $\Phi_{2d}$ is magnetic flux piercing the coil 2d, $\Phi_{2e}$ is magnetic flux piercing the coil 2e, and $\Phi_{2f}$ is magnetic flux piercing the coil 2f.

In other words, the pick-up coil 2 in the present embodiment is a pick-up coil that conducts the second-order differential in an axis direction (vertical direction) of the bobbins 21a (the first term) and 21b (the second term) and simultaneously conducts the first-order differential in the horizontal direction. In this way, the pick-up coil 2 detects the magnetic signal subjected to the second-order differential in the vertical direction and in addition subjected to the first-order differential in the horizontal direction. Therefore, the environmental magnetic field can be reduced as compared with the case where the second-order differential type pick-up coil is used.

In the pick-up coils shown in FIG. 8 and FIG. 9, the coil shape is circular. However, this is not restrictive. For example, polygonal coils may be used.

An example of a pick-up coil arrangement method in the present embodiment will now be described with reference to FIGS. 10, 11A and 11B together with FIG. 9.

Figure 10:
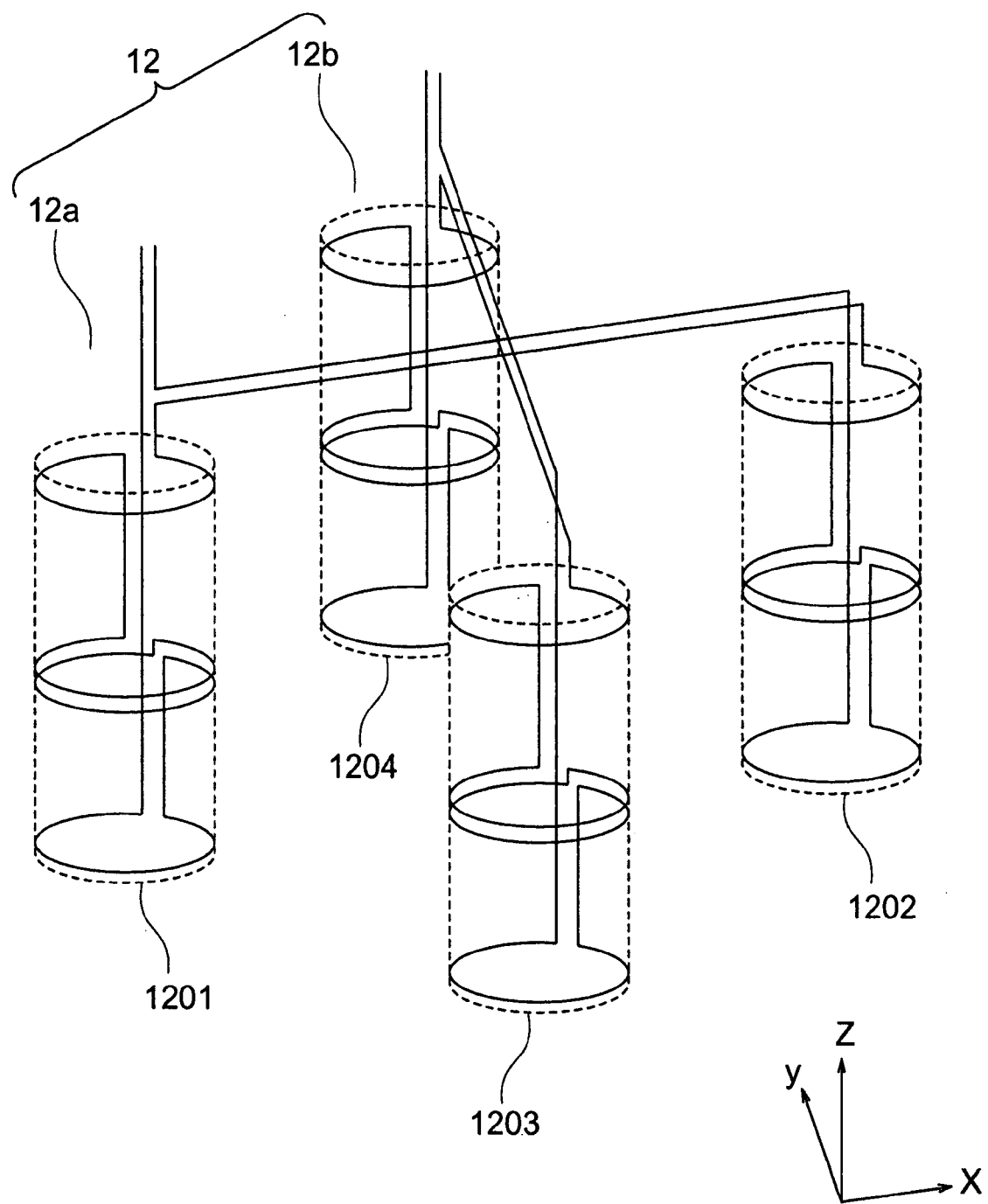
FIG. 10 is an oblique view showing arrangement of a pick-up coil in the embodiment.

FIG. 10 is an oblique view showing arrangement of a pick-up coil in the present embodiment.

Each of pick-up coils 12a and 12b has the same configuration as that of the pick-up coil 2 shown in FIG. 9. In other words, either of the pick-up coils 12a and 12b has a configuration including one pair of differential type coils. The pick-up coil 12a includes a coil 1201 having a configuration of the second-order differential type pick-up coil, and a coil 1202 having a winding direction opposite to that of the coil 1201. In the same way, the pick-up coil 12b includes a coil 1203 having a configuration of the second-order differential type pick-up coil, and a coil 1204 having a winding direction opposite to that of the coil 1203. The set of the pick-up coils 12a and 12b is referred to as pick-up coil set 12. The pick-up coil set 12 has a feature that the pick-up coils 12a and 12b are arranged with directions of the first-order differential in the horizontal direction being perpendicular to each other.

Figure 11A:
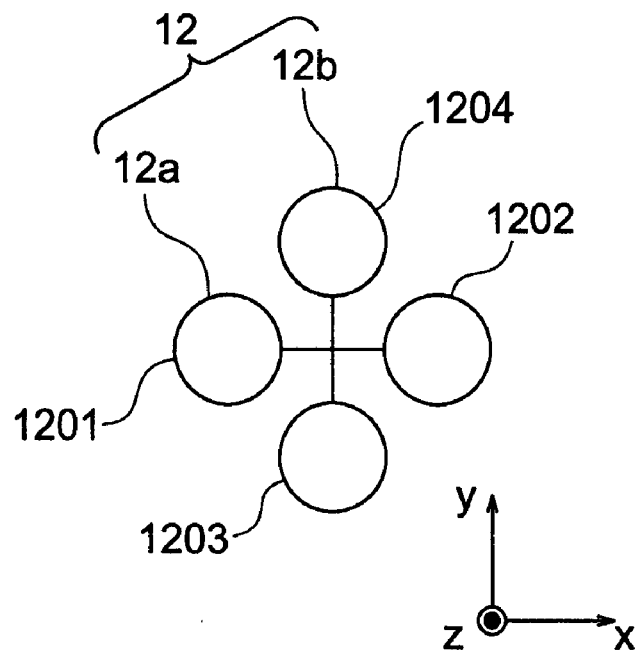
FIG. 11A is a top view schematically showing the set of the pick-up coils shown in FIG. 10.
Figure 11B:
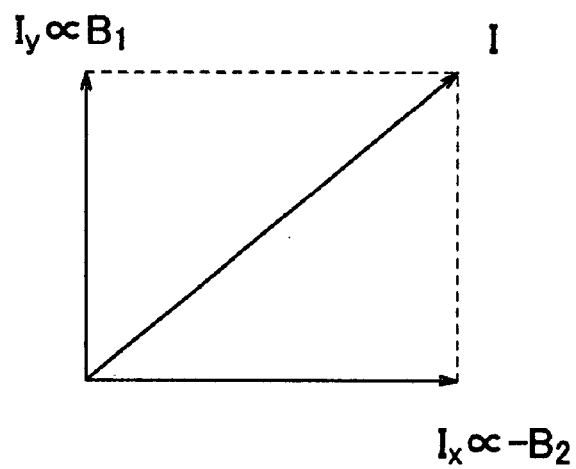
FIG. 11B is a diagram showing relations among a current vector which is a magnetic source, a z-direction magnetic flux density subjected to the first-order differential in the x-axis direction which is detected by a pick-up coil and, and a z-direction magnetic flux density subjected to the first-order differential in the y-axis direction which is detected by a pick-up coil.

FIG. 11A is a top view schematically showing the pick-up coil set shown in FIG. 10. FIG. 11B is a diagram showing relations among a current vector which is a magnetic source, a z-direction magnetic flux density $B_1$ subjected to the first-order differential in the x-axis direction which is detected by the pick-up coil 12a and, and a z-direction magnetic flux density $B_2$ subjected to the first-order differential in the y-axis direction which is detected by the pick-up coil 12b.

Typically, when a current such as a myocardium current is flowing in a sense of the x-axis direction, a magnetic signal can be detected by using pick-up coils for differentiating in the y-axis direction in FIG. 11A and a magnetic field generated by the current can be detected. On the other hand, in the case where pick-up coils for differentiating in the x-axis direction are used, it is desirable to use pick-up coils for differentiating in a direction perpendicular to the sense of the current serving as the magnetic field source. In the case where the sense of the current to be measured is not known beforehand as in the myocardium current, however, it is desirable to dispose two pick-up coils in the present embodiment at right angles as in the pick-up coil set 12 shown in FIG. 10.

In addition, supposing that the magnetic flux density detected by the pick-up coils 12a is $B_1$ and the magnetic flux density detected by the pick-up coils 12b is $B_2$, a vector sum of them can be calculated by the following expression.

$$B_0 = \sqrt{(B_1^2 + B_2^2)} \quad \text{(Expression 3)}$$

By calculating the (Expression 3), it becomes possible to positively detect the magnetic field generated by the current source regardless of the sense of the current source to be measured.

Supposing that the current vector serving as the magnetic field source is $I = (I_x, I_y)$, the x component $I_x$ of the current and the y component $I_y$ of the current can be represented approximately by the following expression by using a change $\Delta B_z / \Delta x$ of a magnetic flux density in the z-direction subjected to the first-order differential in the x-axis direction and a change $\Delta B_z / y$ of a magnetic flux density in the z-direction subjected to the first-order differential in the y-axis direction (see H. Hosaka and D. Cohen, "Visual determination of generators of the magnetocardiogram," Journal of Electrocardiology (USA), 1976, Vol. 9, pp. 426-432).

$$(I_x, I_y) \propto (-\Delta B_z/\Delta y, \Delta B_z/\Delta x) \quad \text{(Expression 4)}$$

Therefore, the x component $I_x$ of the current serving as the magnetic field source and the y component $I_y$ of the current can be represented approximately by the following expression by using a z-direction magnetic flux density $B_1$ subjected to the first-order differential in the x-axis direction which is detected by the pick-up coil 12a and, and a z-direction magnetic flux density $B_2$ subjected to the first-order differential in the y-axis direction which is detected by the pick-up coil 12b.

$$(I_x, I_y) \propto (-B_2, B_1) \quad \text{(Expression 5)}$$

As a result, the pick-up coil set 12 can detect the current serving as the magnetic field source approximately as a current vector. In other words, the current can be represented as a vector by using the magnetic flux densities $B_1$ and $B_2$ respectively detected by the pick-up coils 12a and 12b as shown in FIG. 11B.

It becomes possible to detect the magnetic field distribution by thus arranging a plurality of pick-up coil sets 12. In addition, it becomes possible to detect distribution of the current vector serving as the magnetic field source (current vector field) by using (Expression 5). As for the magnetoencephalography, therefore, it becomes possible to presume a place where a nerve current flows without caring about the direction in which the nerve current is flowing.

Figure 12:
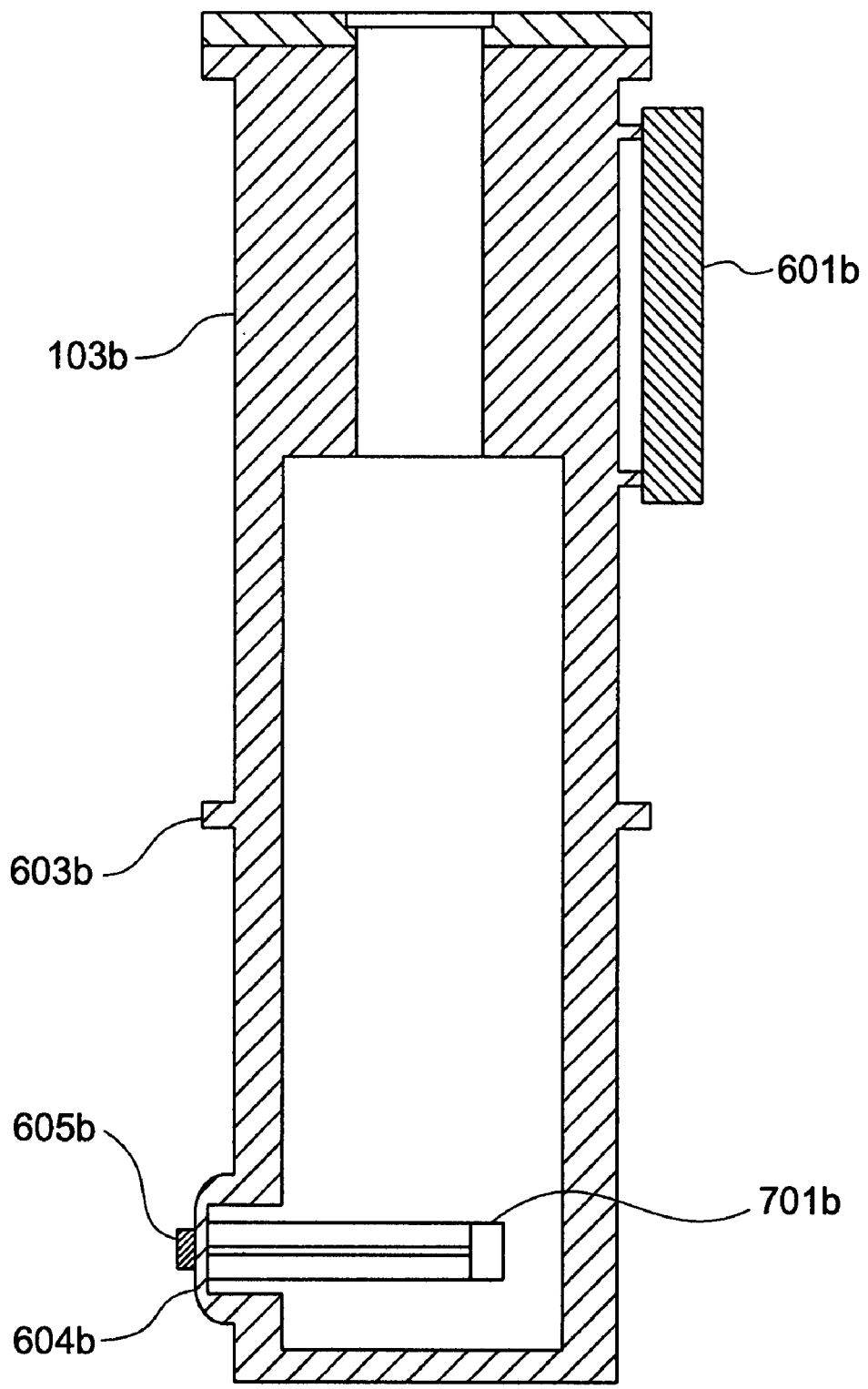
FIG. 12 is a sectional view showing a cryostat in the embodiment.

FIG. 12 is a sectional view taken along a C-C section of FIG. 7C and shows the cryostat in the present embodiment. The inside of the cryostat 103b is filled with liquid helium and thermally insulated from the outside by a vacuum layer. A pick-up coil set 701b has the same configuration as that of the pick-up coil set 12 shown in FIG. 10. Respective pick-up coils are arranged so that pick-up coil planes will become parallel to the pick-up plane 604b of the cryostat 103b. In the cryostat 103b, its inner layer, outer layer and vacuum layer are worked to be thinner at the pick-up plane 604b as compared with other portions. This brings about an effect that the distance between the pick-up coil planes and the signal source becomes small and the signal strength becomes large.

The pick-up plane 604b has a pressure sensor 605b, and pressure between the body surface of the subject and the pick-up plane 604b can be measured. Owing to this configuration, it becomes possible to detect, for example, that the pick-up plane has come in contact with the body surface. Furthermore, by previously setting a threshold, it is possible to sound an alarm or automatically stop the apparatus when a pressure that is at least the threshold is applied.

FIGS. 13A-13D and FIGS. 14A-14C are diagrams showing location relations between the head and the cryostats at the time of magnetoencephalography (cerebral magnetic field) measurement in the present embodiment.

Figure 13A:
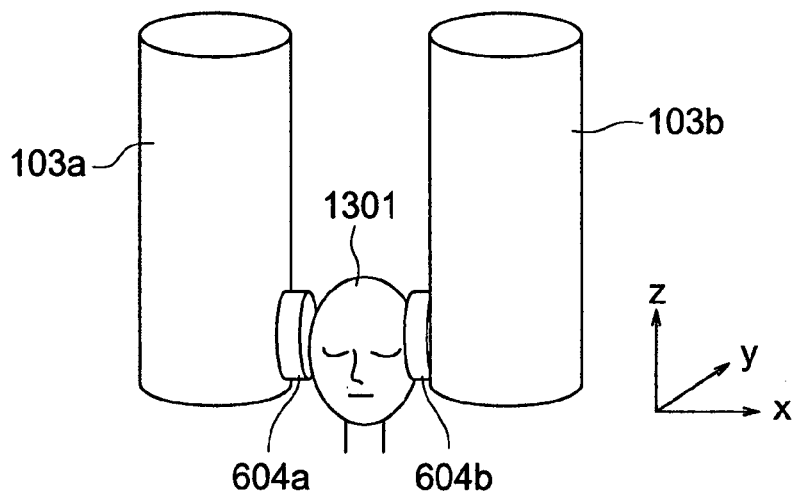
FIGS. 13A-13D are diagrams showing location relations between a head and cryostats at the time of magnetoencephalography (cerebral magnetic field) measurement in the embodiment.
Figure 13B:
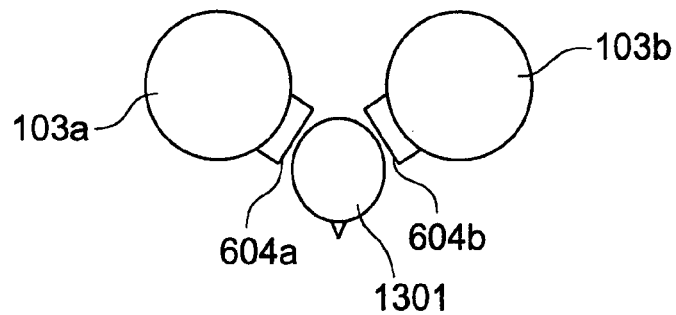
Figure 13C:
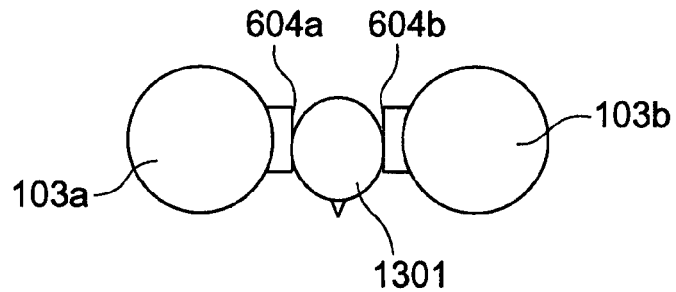
Figure 13D:
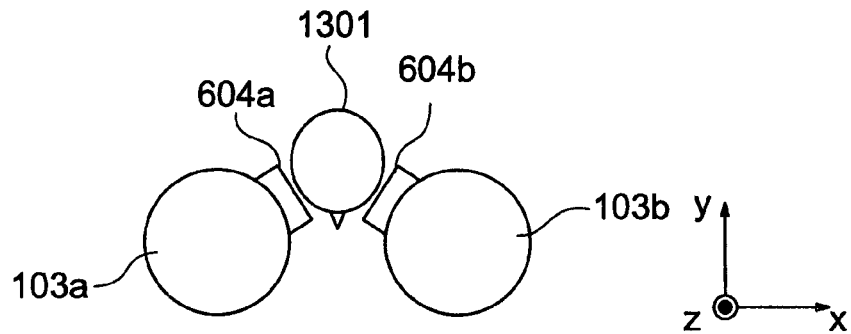

FIGS. 13A-13D show location relations between the head and the cryostats when magnetoencephalography measurement is conducted on a subject 1301 in the sedentary position or erect position. FIG. 13A is an oblique view showing location relations between the head and the cryostats when magnetoencephalography measurement is conducted near the temples of the subject 1301. FIGS. 13B-13D are top views showing location relations between the head and the cryostats at the time of magnetoencephalography measurement. FIG. 13B shows location relations between the head and the cryostats at the time of magnetoencephalography measurement near the occipital region of the subject 1301. FIG. 13C shows location relations between the head and the cryostats at the time of magnetoencephalography measurement near the temples of the subject 1301. FIG. 13D shows location relations between the head and the cryostats at the time of magnetoencephalography measurement near the forehead of the subject 1301.

Figure 14A:
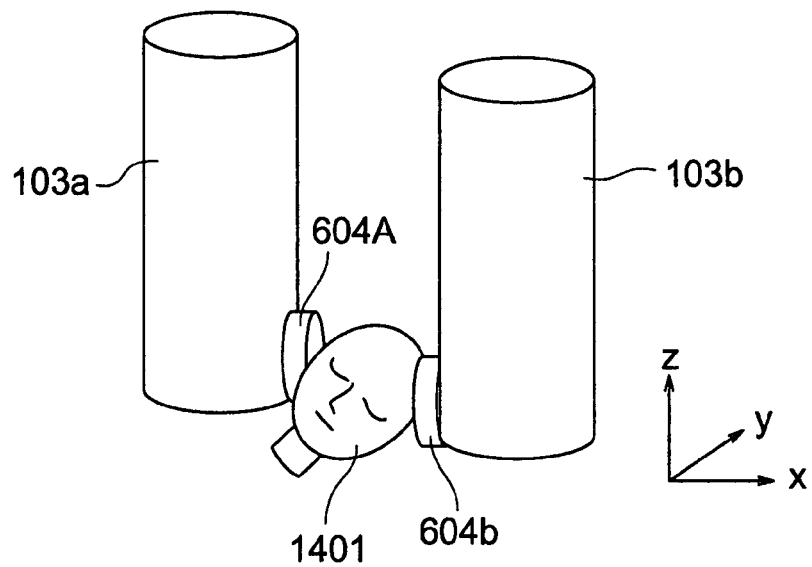
FIGS. 14A-14C are diagrams showing location relations between a head and cryostats at the time of magnetoencephalography measurement in the embodiment.
Figure 14B:
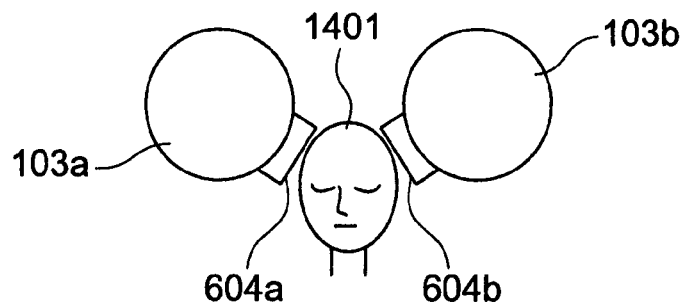
Figure 14C:
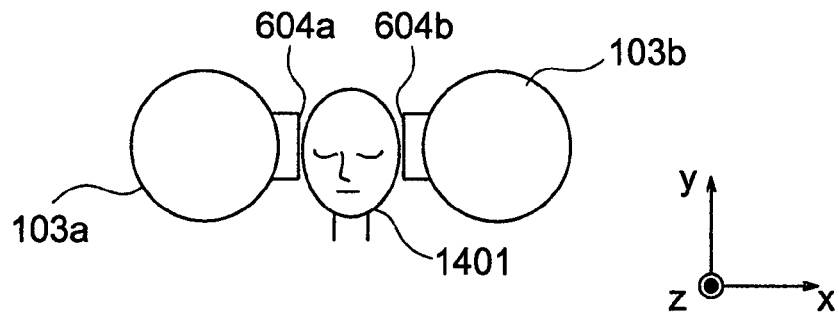

FIGS. 14A-14C show location relations between the head and the cryostats when magnetoencephalography measurement is conducted on a subject 1401 in the supine position or prone position. FIG. 14A is an oblique view showing location relations between the head and the cryostats when magnetoencephalography measurement is conducted near the temples of the subject 1401. FIGS. 14B and 14C are top views showing location relations between the head and the cryostats at the time of magnetoencephalography measurement. FIG. 14B shows location relations between the head and the cryostats at the time of magnetoencephalography measurement near the vertex of the subject 1401. FIG. 14C shows location relations between the head and the cryostats at the time of magnetoencephalography measurement near the temples of the subject 1401.

It becomes possible to fit the pick-up planes to all locations of the head of the subject by thus interlocking the two cryostats 103a and 103b with each other and moving them in the vertical, lateral and rotational directions with the bilateral symmetry relation maintained. Furthermore, since the cryostats are necessarily in the bilateral symmetry relation, it becomes possible to easily square locations of the pick-up planes 604a and 604b with locations of regions that are bilaterally symmetrical in the head. According to this configuration, it becomes possible to measure magnetoencephalography signals in corresponding regions in the left brain and the right brain simultaneously.

Figure 15A:
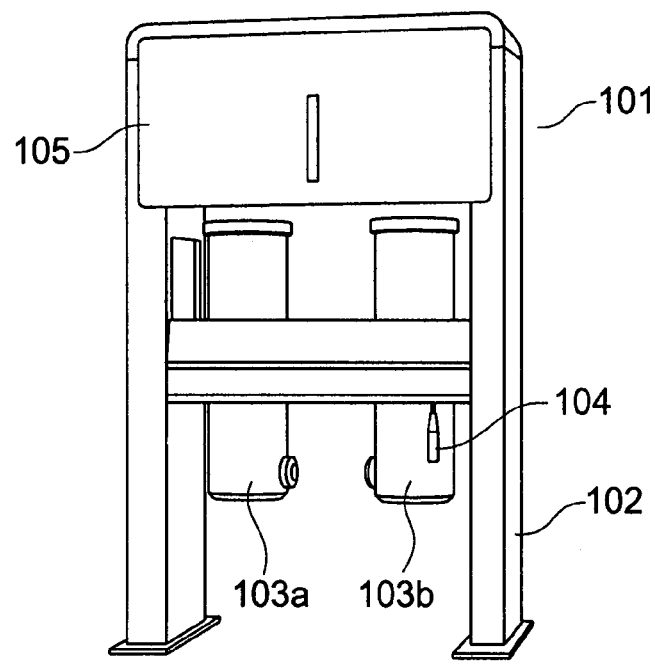
Figure 15B:
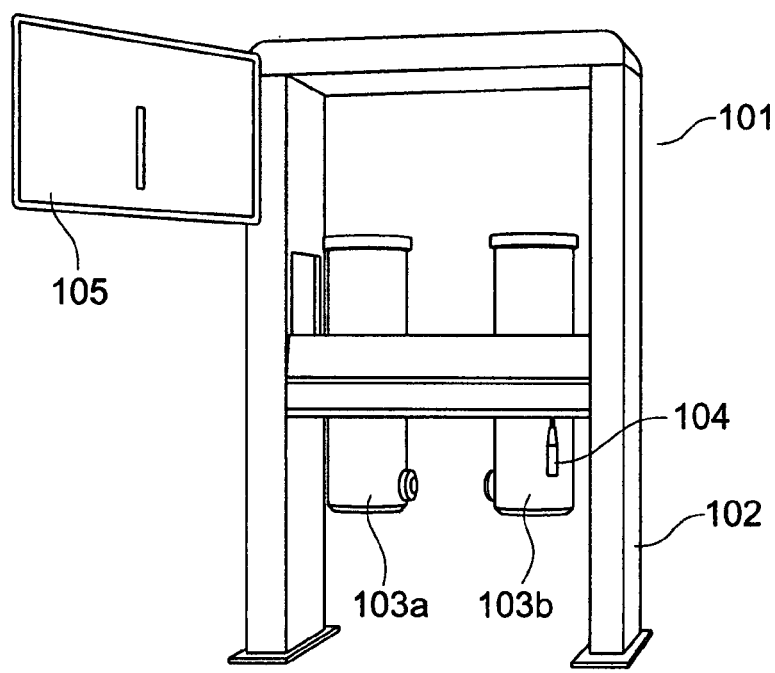

FIGS. 15A and 15B are oblique views showing a movement of the gantry at the time of cryostat maintenance in the present embodiment. FIG. 15A is a view showing a state in which the second support 106 (see FIG. 5) is lowered most. FIG. 15B is a view showing a state in which the gantry front cover 105 is opened. As for the maintenance of the cryostats 103a and 103b, there are mainly vacuum evacuation work and liquid helium filling work. In the present embodiment, it is made unnecessary to remove the gantry front cover 105 by fixing the gantry front cover 105 to the gate type support 102 by using hinges and opening the gantry front cover 105 on the hinges. Owing to this hinge structure, maintenance of the cryostats 103a and 103b can be conducted more simply.

When removing the cryostats from the gantry in the present embodiment, it is necessary to draw out the cryostats 103a and 103b upward. For drawing out the cryostats 103a and 103b upward, it is necessary to lower the second support 106 as shown in FIG. 15B. The cryostats 103a and 103b can be removed from the gantry easily by sufficiently lowering the second support 106.

Figure 16:
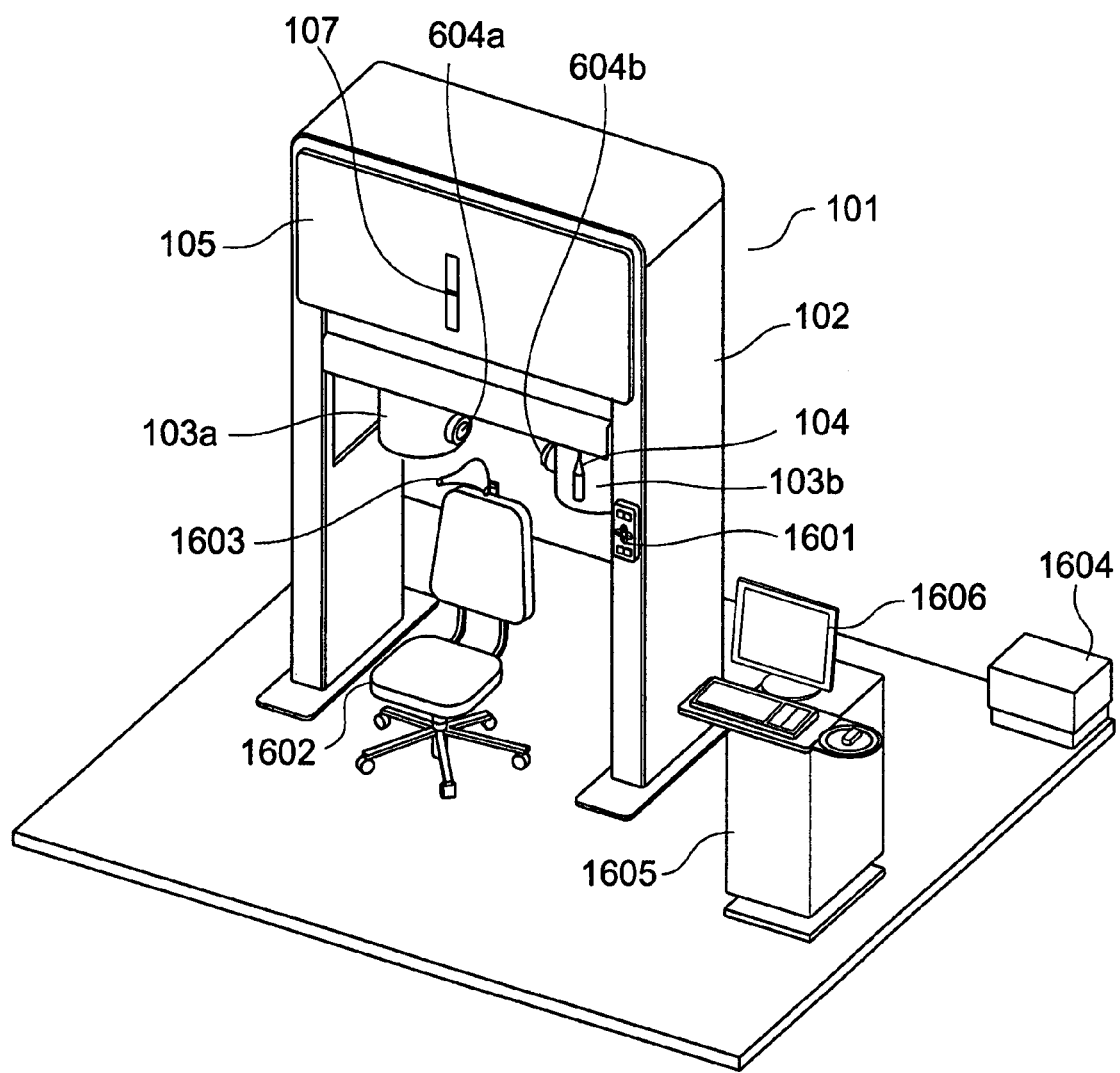
FIG. 16 is an oblique view showing a cerebral magnetic field measurement apparatus in the embodiment.

FIG. 16 is an oblique view showing a cerebral magnetic field measurement apparatus in the present embodiment.

The pick-up coil 1 shown in FIG. 8 or the pick-up coil 2 shown in FIG. 9 and the SQUID are kept at temperatures equal to or lower than the superconducting transition temperature of a superconducting substance that forms the SQUID in the cryostats 103a and 103b. Specifically, the inside of each of the cryostats 103a and 103b is filled with liquid helium and thermally insulated from the outside by a vacuum layer. In the present embodiment, two pick-up coils 2 each shown in FIG. 9 is arranged as the pick-up coil set 12 shown in FIG. 10. The pick-up coils are arranged so that the pick-up coil planes will become parallel to the pick-up planes 604a and 604b respectively of the cryostats 103a and 103b, respectively.

The cryostats 103a and 103b are supported by the gantry. The cryostats 103a and 103b are driven in the vertical direction by the gantry. Furthermore, the cryostats 103a and 103b are interlocked with each other and driven at the same velocity in the horizontal direction so as to bring them closer to each other or make them go away from each other. Furthermore, the cryostats 103a and 103b are driven to rotate (clockwise or counterclockwise) in the horizontal plane. At this time, the cryostats 103a and 103b are interlocked with each other and driven to rotate at the same rotation velocity respectively in directions that are opposite to each other. Drive of the cryostats 103a and 103b is conducted by controlling hydraulic pumps. Specifically, pressure is transmitted to hydraulic cylinders installed on the gantry by controlling electromagnetic valves in a hydraulic control device 1604 from a controller 1601. As a result, the drive means 501, 502a, 502b, 503a and 503b on the gantry shown in FIG. 5 are driven.

A head rest 1603 is installed on a chair 1602 on which the subject sits, in order to fix the head of the subject. The pick-up planes 604a and 604b respectively of the cryostats 103a and 103b are regulated so as to approach the head of the subject by using the controller 1601. The spacing between the pick-up planes 604a and 604b can be widened quickly by pulling the lever 104 near side.

The SQUID fluxmeters are controlled and magnetic signals detected by pick-up coils are converted to voltage signals and transmitted to a signal processing device 1605 by FLL circuits 601a and 601b respectively fixed to the cryostats 103a and 103b. The signal processing device 1605 conducts processing of removing a noise signal by using the DSP, detects the magnetoencephalography signal of the subject, and displays a magnetoencephalography waveform on a display device 1606 in real time. In order to measure the transmission time of the nerve, the transmission time can be displayed in real time by giving audio stimuli to an ear of the subject with an auditory sense stimulating device, monitoring the reaction in real time and calculating a time difference between peaks from the magnetoencephalography waveform. The spontaneous cerebral magnetic field and event-related cerebral magnetic field can also be measured, besides sensory evoked cerebral magnetic field caused by a response of the auditory stimulation, visual stimulation or somatosensory stimulation.

Figure 17:
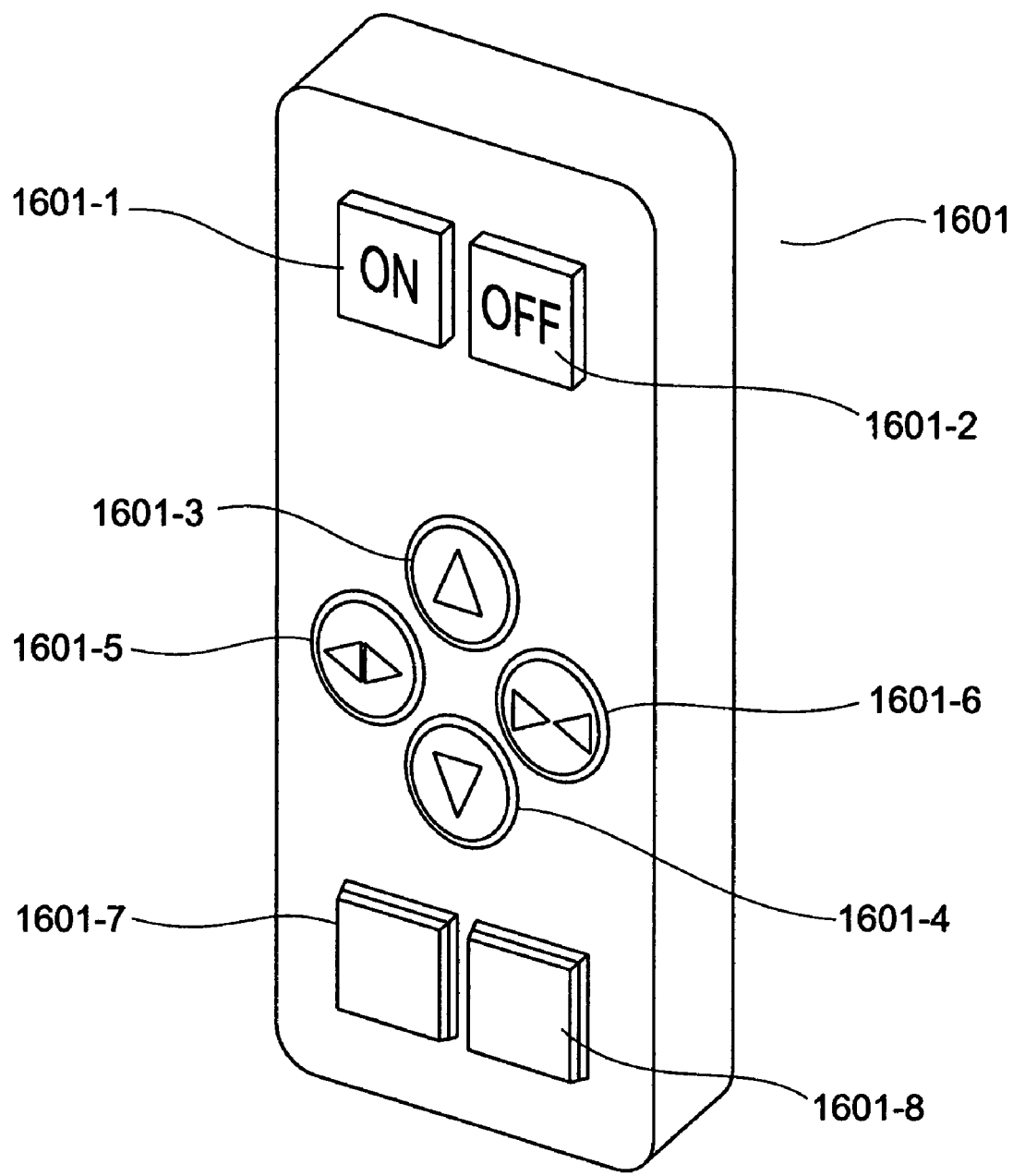
FIG. 17 is an oblique view showing a controller for operating the gantry in the embodiment.

FIG. 17 is an oblique view showing the controller 1601 for operating the gantry in the present embodiment. At the time of measurement, an ON switch 1601-1 is depressed to turn on power of the hydraulic control device 1604. The cryostats 103a and 103b are interlocked with each other and driven upward, by depressing an operation button 1601-3. The cryostats 103a and 103b are interlocked with each other and driven downward, by depressing an operation button 1601-4. The cryostats 103a and 103b are interlocked with each other and driven so as to go away from each other in the horizontal direction, by depressing an operation button 1601-5. The cryostats 103a and 103b are interlocked with each other and driven so as to get nearer to each other in the horizontal direction, by depressing an operation button 1601-6. The cryostats 103a and 103b are interlocked with each other and driven to rotate at the same rotation velocity respectively clockwise and counterclockwise, by depressing an operation button 1601-7. On the contrary, the cryostats 103a and 103b are interlocked with each other and driven to rotate at the same rotation velocity respectively counterclockwise and clockwise, by depressing an operation button 1601-8. When terminating the measurement, power of the hydraulic control device 1604 is turned off by depressing an OFF switch 1601-2.

Figure 18:
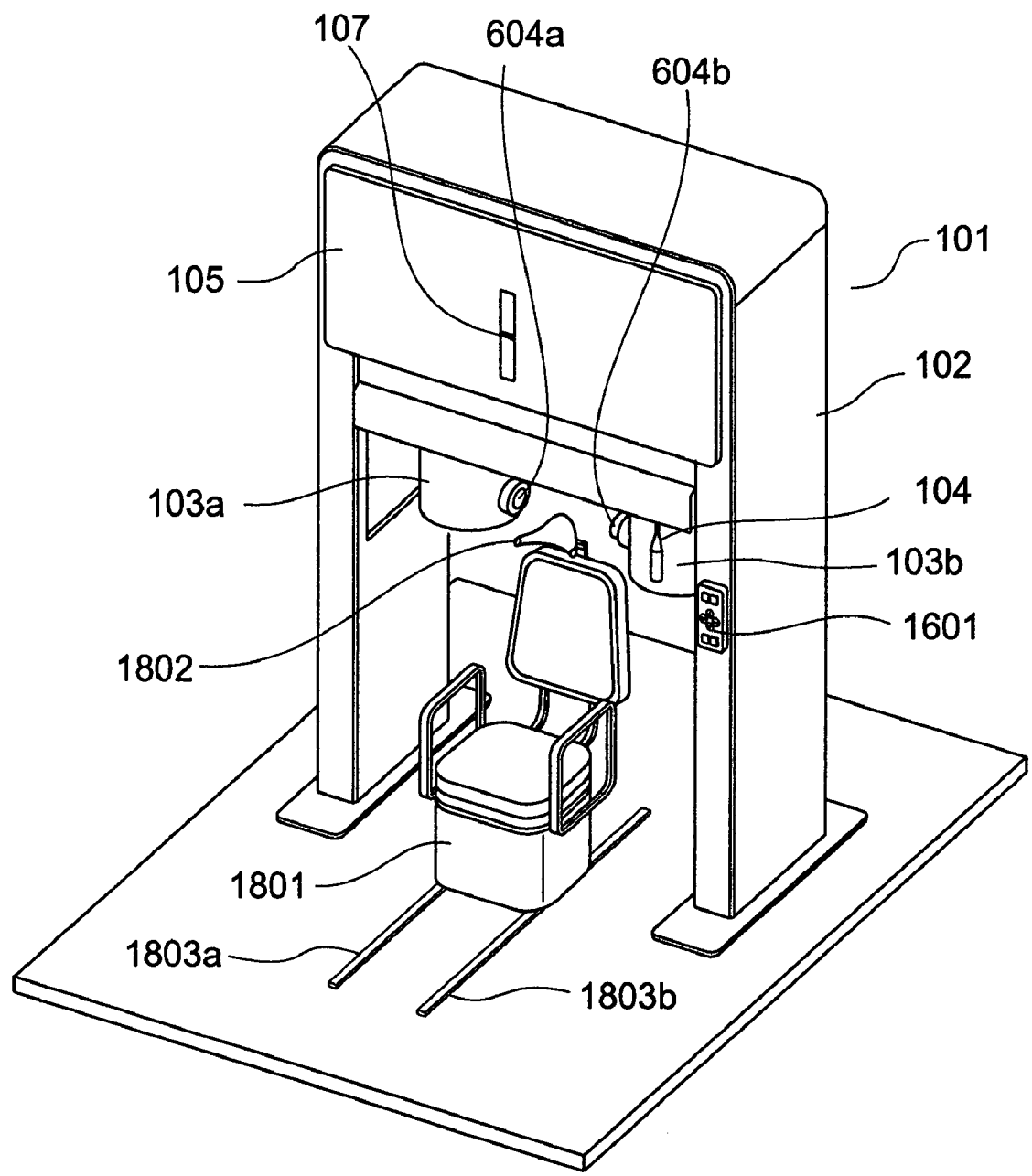
FIG. 18 is an oblique view showing a cerebral magnetic field measurement apparatus in the embodiment.

FIG. 18 is an oblique view showing a cerebral magnetic field measurement apparatus in the present embodiment. The magnetic field measurement apparatus shown in FIG. 18 has a configuration obtained from the magnetic field measurement apparatus shown in FIG. 16 by replacing the chair 1602 with a chair 1801 which moves horizontally on rails 1803a and 1803b. The chair 1801 has a mechanism for moving the chair 1801 on the rails 1803a and 1803b so as to pass the head through the center of the two cryostats 103a and 103b in a back-forth direction, i.e., in a direction perpendicular to paper in FIG. 2A. The present configuration brings about an effect that the head of the subject can be easily squared in location with the two cryostats 103a and 103b.

Figure 19:
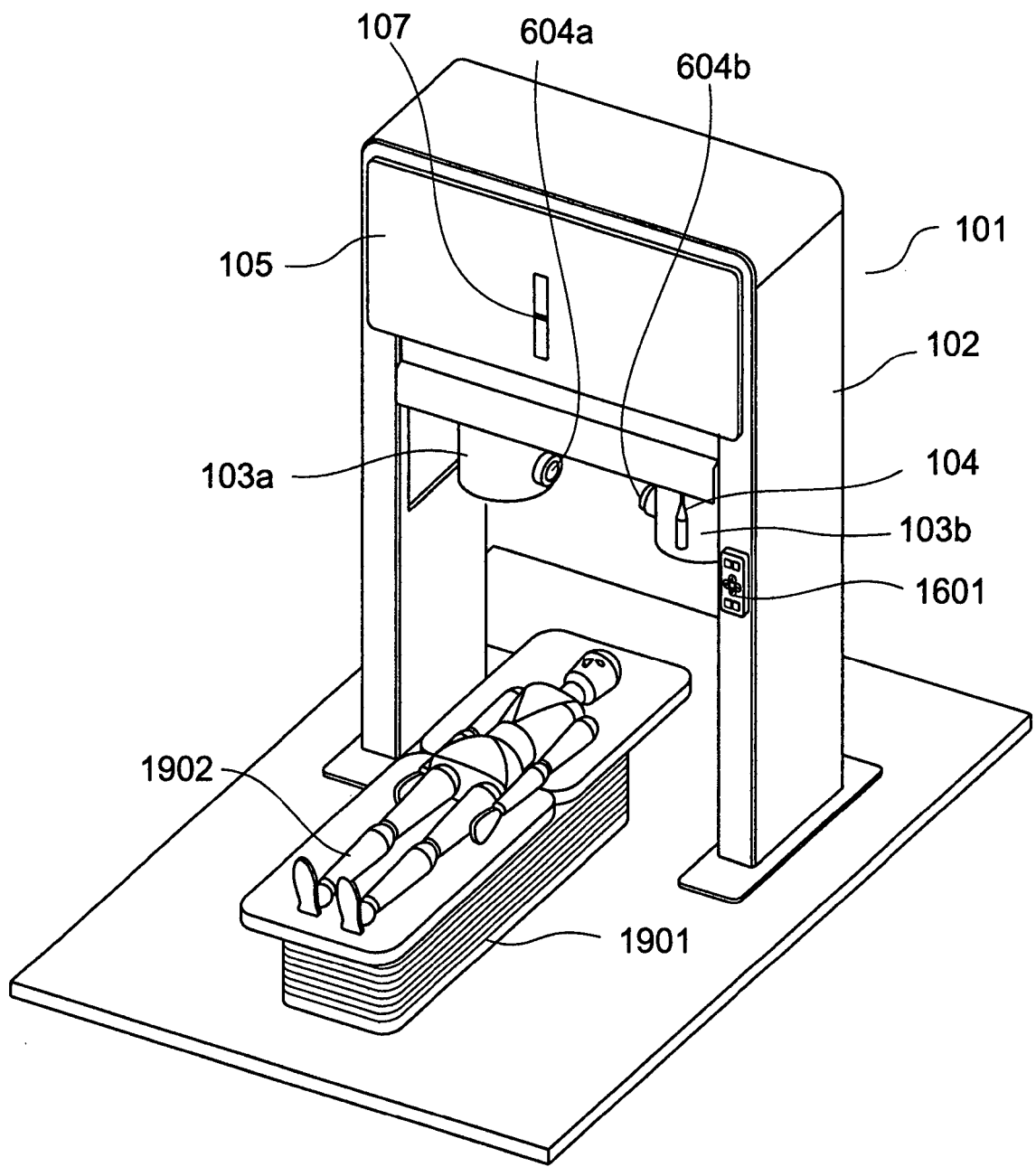
FIG. 19 is an oblique view showing a cerebral magnetic field measurement apparatus in the embodiment.

FIG. 19 is an oblique view showing a cerebral magnetic field measurement apparatus in the present embodiment. The magnetic field measurement apparatus shown in FIG. 19 has a configuration obtained from the magnetic field measurement apparatus shown in FIG. 16 by replacing the chair 1602 with a bed 1901. The bed 1901 has a mechanism for moving the chair 1801 on the rails 1803a and 1803b so as to pass the head through the center of the two cryostats 103a and 103b in a back-forth direction, i.e., in a direction perpendicular to paper in FIG. 2A, a mechanism for moving a bed board in the vertical direction, and a reclining mechanism. According to the present configuration, measurement can be conducted on the subject in the supine position as represented by a subject 1902, and measurement in the states shown in FIGS. 14A-14C is possible. Furthermore, measurement of the subject in the sedentary position can also be conducted by raising up a part of the bed board by using the reclining mechanism. In addition, the present configuration brings about an effect that the head of the subject can be easily squared in location with the center of the two cryostats 103a and 103b in any state.

FIGS. 20 to 23 are diagrams showing screens displaying signals obtained by the cerebral magnetic field measurement apparatus in the present embodiment.

Figure 20:
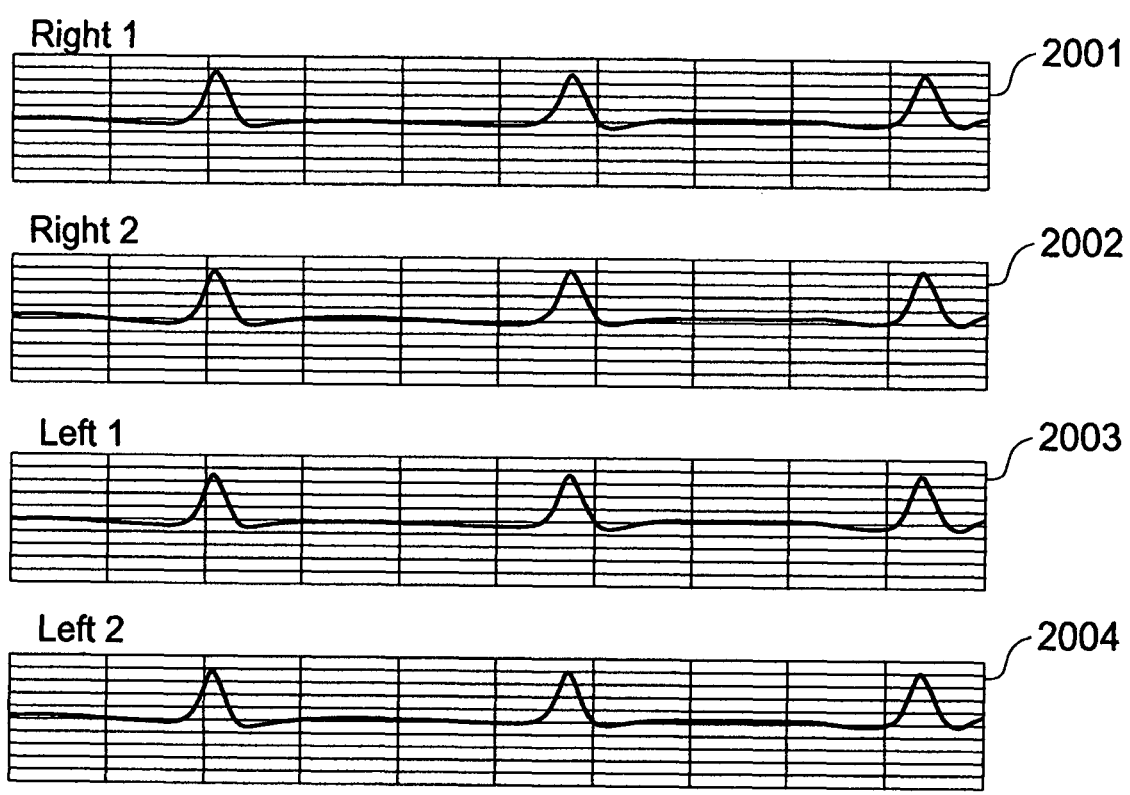
FIG. 20 is graphs showing temporal waveforms obtained from four sensors.

FIG. 20 is a graph showing temporal waveforms obtained from four sensors. The abscissa axis of each graph indicates time, and the ordinate axis indicates an output signal (magnetic field) of each SQUID fluxmeter. Waveforms 2001 and 2002 represent a magnetic field (Right 1) detected by a first pick-up coil held in the cryostat 103a and a magnetic field (Right 2) detected by a second pick-up coil held in the cryostat 103a, respectively. Waveforms 2003 and 2004 represent a magnetic field (Left 1) detected by a third pick-up coil held in the cryostat 103b and a magnetic field (Left 2) detected by a fourth pick-up coil held in the cryostat 103b, respectively. This display can represent the simplest magnetic field change.

Figure 21:
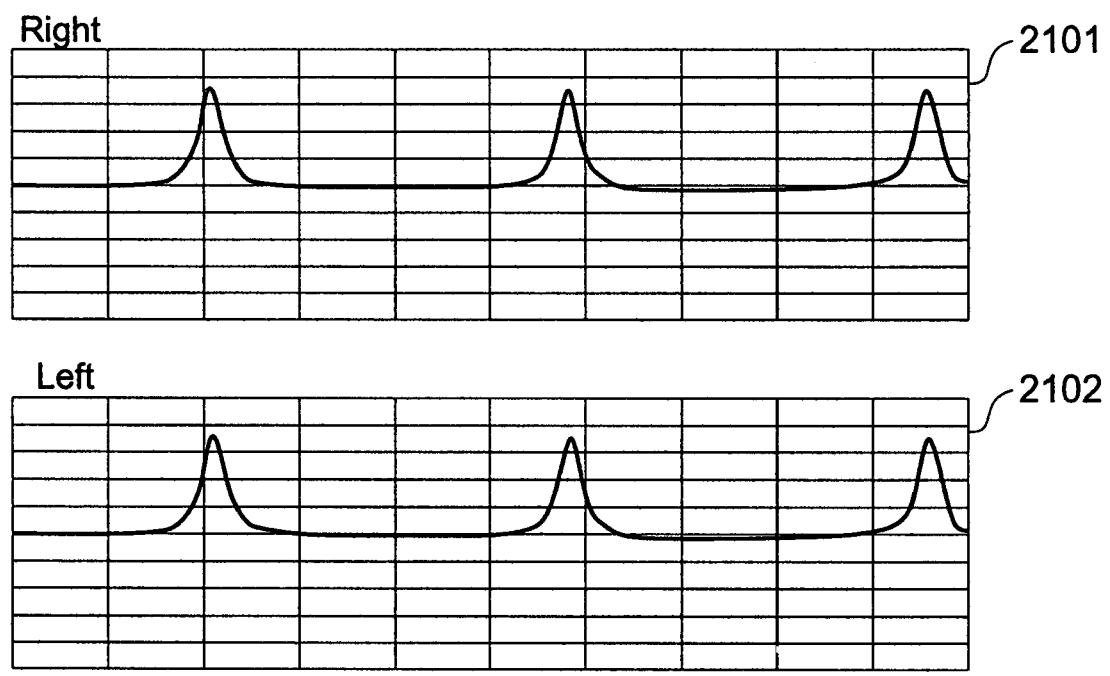
FIG. 21 is graphs showing temporal waveforms of signals obtained by conducting vector addition on magnetic fields detected by two pick-up coils held in each cryostat.

FIG. 21 is graphs showing temporal waveforms of signals obtained by conducting vector addition on outputs of two sensors held in each cryostat. The abscissa axis of each graph indicates time, and the ordinate axis indicates a vector sum of output signals (magnetic fields) of two SQUID fluxmeters held in each cryostat. A waveform 2101 represents a vector sum obtained by compounding the magnetic field (Right 1) detected by the first pick-up coil held in the cryostat 103a and the magnetic field (Right 2) detected by the second pick-up coil held in the cryostat 103a with (Expression 3). A waveform 2102 represents a vector sum obtained by compounding the magnetic field (Left 1) detected by the third pick-up coil held in the cryostat 103b and the magnetic field (Left 2) detected by the fourth pick-up coil held in the cryostat 103b with (Expression 3). This display method is suitable for detecting waveform peaks. For example, it is facilitated to detect the time of peak, find the period of the waveform, or a trigger signal of the averaging.

Figure 22:
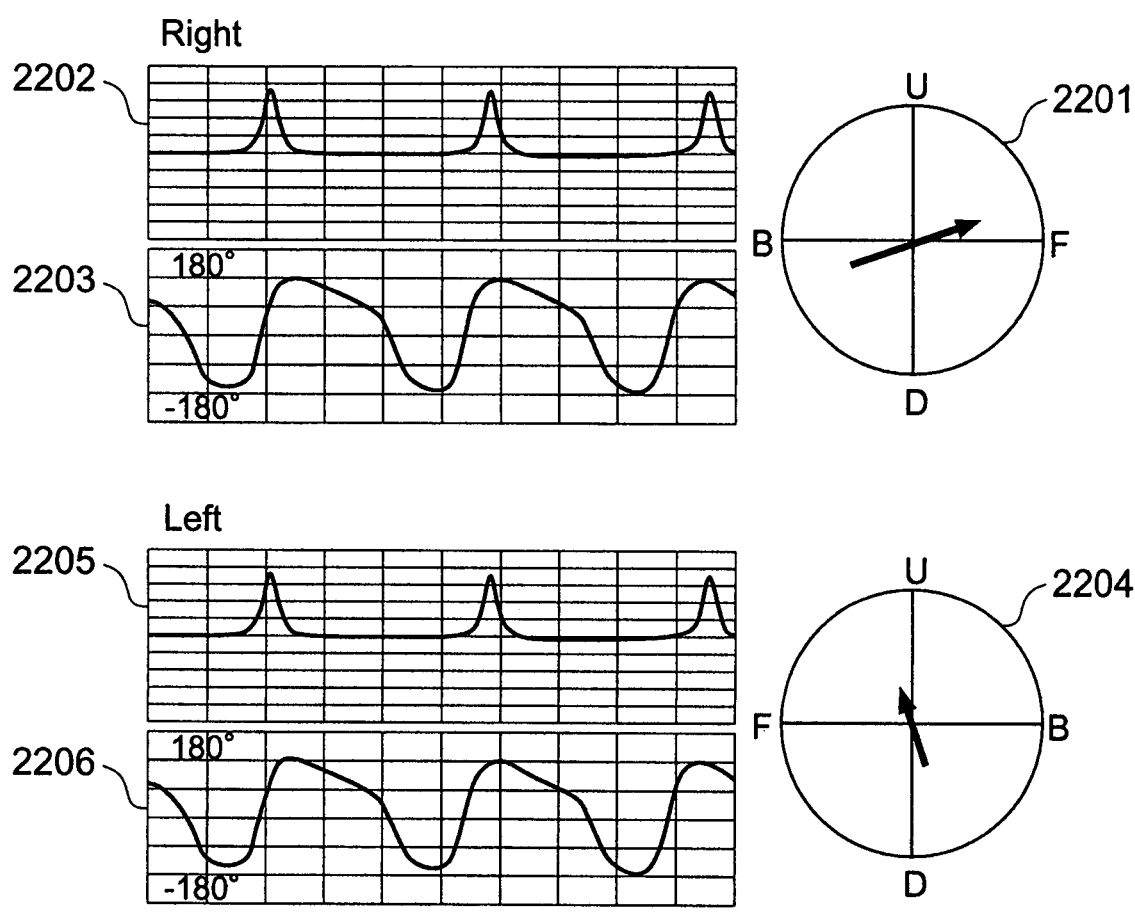
FIG. 22 is graphs each showing magnetic fields detected by two pick-up coils held in each cryostat, as a current vector and graphs each showing temporal waveforms of magnitude and phase of the current vector.

FIG. 22 shows graphs each representing outputs of the two sensors held in each cryostat, as a current vector and graphs each showing temporal waveforms of magnitude and phase of the current vector. A current vector 2201 is a vector representing the sense and magnitude of a current calculated by using (Expression 5) and magnetic fields (Right 1 and Right 2) detected by two pick-up coils held in the cryostat 103a. A waveform 2202 is the same waveform as the waveform 2101 shown in FIG. 21, and corresponds to the magnitude of the current vector 2201. A waveform 2203 indicates the phase of the current vector 2201. The abscissa axes of the graphs of the waveform 2202 and the waveform 2203 indicate time.

In the same way, a current vector 2204 is a vector representing the sense and magnitude of a current calculated by using (Expression 5) and magnetic fields (Left 1 and Left 2) detected by two pick-up coils held in the cryostat 103b. A waveform 2205 is the same waveform as the waveform 2102 shown in FIG. 21, and corresponds to the magnitude of the current vector 2204. A waveform 2206 indicates the phase of the current vector 2204. The abscissa axes of the graphs of the waveform 2205 and the waveform 2206 indicate time. The magnitude and sense of the nerve current can be confirmed intuitively by the current vector indication. Furthermore, the magnitude and sense of the nerve current can be measured quantitatively by indicating the magnitude and phase of the current vector quantitatively. In other words, use of the present indication method brings about an effect that the magnitude and sense of the nerve current of each subject are converted into numerical values for comparison among subjects.

Figure 23:
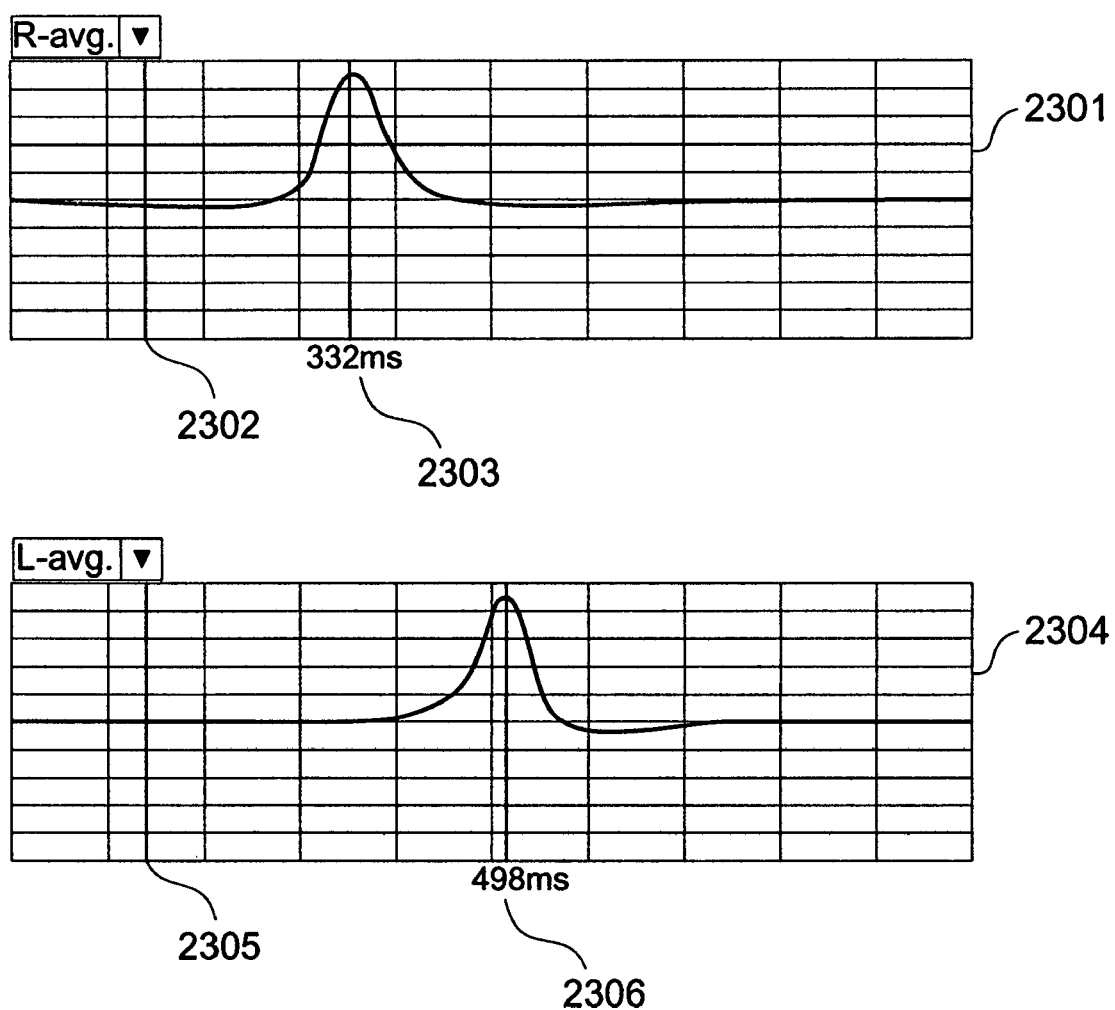
FIG. 23 is graphs each showing a waveform obtained by conducting averaging on signals obtained from magnetic fields detected by two pick-up coils held in each cryostat.

FIG. 23 is graphs showing waveforms obtained by conducting averaging on signals obtained from outputs of the two sensors held in each cryostat. The graphs are obtained by conducting averaging on the signals obtained from the cryostats 103a and 103b in response to input of an auditory sense stimulation signal serving as a trigger. Here, an example obtained by conducting magnetoencephalography measurement with the pick-up plane 604a of the cryostat 103a brought close to the right head of the subject and the pick-up plane 604b of the cryostat 103b brought close to the left head of the subject. FIG. 23 shows graphs respectively obtained by conducting averaging on vector sum waveforms shown in FIG. 21. At time 2302 and 2305, auditory sense stimulation is given by causing the subject to hear a pulse sound. Time 2303 and 2306 represent peak time points of obtained waveforms. A signal having a high S/N ratio can be detected by thus conducting the averaging. In addition, it becomes possible to detect the transmission time of the cerebral nerve by comparing the magnetic signal of the right brain obtained from the SQUID fluxmeter in the cryostat 103a with the magnetic signal of the left brain obtained from the SQUID fluxmeter in the cryostat 103b. It is anticipated to quantify a change in the cerebral function caused by a cerebral disease or senility by detecting the transmission time of the cerebral nerve.

The pick-up coil in the present embodiment has been described heretofore by taking a pick-up coil that conducts the first-order differential or the second-order differential in the vertical direction as an example. However, the pick-up coil in the present embodiment has a configuration for detecting a signal differentiated in two different directions. For example, a pick-up coil that conducts at least the third integral in the vertical direction may also be used.

The embodiment has heretofore described by taking the SQUID fluxmeter as an example of the fluxmeter for converting the magnetic flux detected by a pick-up coil to a voltage value. Alternatively, other fluxmeters such as magnetoresistive elements, giant magnetoresistive elements, flux gate fluxmeters or optical pumping fluxmeters may be used as the fluxmeters. Furthermore, the example in which the SQUID is cooled by using liquid helium has been described. Alternatively, a refrigerator may be used. Or if the SQUID is formed of a high temperature superconducting member, it may be cooled by using liquid nitrogen.

According to the present embodiment, it becomes possible to easily square the head of the subject in location with the pick-up plane. In addition, a biomagnetic field measuring apparatus capable of simply detecting cerebral magnetic signals generated from relating regions in the left brain and the right brain can be implemented by conducting the magnetoencephalography measurement on two points of the head part in the bilateral symmetry relation.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:
1. A biomagnetic field measurement apparatus comprising:
a gate-type first support including two leg parts and a coupling part coupling upper parts of the two leg parts;

a first and a second cylindrical cryostats disposed side by side between the two leg parts and under the coupling part;

a first and a second pick-up sensors configured to detect biomagnetic fields, the first and the second pick-up sensors being disposed in mirror symmetric locations, the first and the second pick-up sensors being incorporated in the first and second cryostats, respectively, and at least a part of the each pick-up sensor being protruded from a side face of a respective cylindrical cryostat;

a second support supported by the first support and configured to drive the two cryostats in an axis direction of the cryostats;

a third support supported by the second support and configured to drive the cryostats in directions along the coupling part;

a fourth support supported by the third support and configured to drive each cryostat to rotate around a respective axis of each cryostat;

drive elements configured to drive, respectively, the second to fourth supports; and a controller configured to control the drive elements.

2. The biomagnetic field measurement apparatus according to claim 1, wherein the drive elements drives the two cryostats between the two leg parts in directions causing the two cryostats to get nearer to each other or go away from each other in synchronization with each other by using the third support, and the drive elements drives the two cryostats to rotate in rotation directions opposite to each other, by using the fourth support.

3. The biomagnetic field measurement apparatus according to claim 1, wherein each of the pick-up sensors transmits a magnetic signal detected by a magnetic pick-up coil comprising a superconductor or a metal member to a superconducting quantum interference device.

4. The biomagnetic field measurement apparatus according to claim 3, wherein the magnetic pick-up coil comprises a superconductor or a metal member, and a plurality of differential type coils having respectively different loop directions are arranged in parallel at predetermined spacing and connected to each other.

5. The biomagnetic field measurement apparatus according to claim 4, wherein the differential type coils are two differential type coils.

6. The biomagnetic field measurement apparatus according to claim 4, wherein the differential type coils are second-order differential type coils.

7. The biomagnetic field measurement apparatus according to claim 4, wherein the differential type coils are first-order differential type coils.

8. The biomagnetic field measurement apparatus according to claim 3, wherein the superconductor or metal member is a wire.

9. The biomagnetic field measurement apparatus according to claim 3, wherein two said magnetic pick-up coils comprise a set of the magnetic pick-up coils crossing each other.

10. The biomagnetic field measurement apparatus according to claim 9, wherein the two magnetic pick-up coils cross at right angles.

11. The biomagnetic field measurement apparatus according to claim 10, wherein a first one of said set of the magnetic pick-up coils incorporated in the first cryostat and a second one of said set of the magnetic pick-up coils incorporated in the second cryostat are disposed in mirror symmetric locations.

12. The biomagnetic field measurement apparatus according to claim 1, wherein the third support has a lever for manually driving the third support.

13. The biomagnetic field measurement apparatus according to claim 1, wherein the first support has a door between the cryostats and a side where a subject is disposed.

14. The biomagnetic field measurement apparatus according to claim 1, further comprising a sensor for measuring disposition of the two cryostats.

15. The biomagnetic field measurement apparatus according to claim 1, wherein a sensor for measuring pressure is disposed on a surface of a projection part of each of the cryostats.

16. The biomagnetic field measurement apparatus according to claim 1, wherein the drive means comprise cylinders.

* * * * *